(12) United States Patent
George et al.

(10) Patent No.: US 12,359,053 B2
(45) Date of Patent: Jul. 15, 2025

(54) FLOW CELL INCLUDING A HETEROPOLYMER

(71) Applicants: ILLUMINA, INC., San Diego, CA (US); ILLUMINA CAMBRIDGE LIMITED, Cambridge (GB)

(72) Inventors: Wayne N. George, Ilford (GB); Ludovic Vincent, San Diego, CA (US); Andrew A. Brown, Cambridge (GB); Mathieu Lessard-Viger, San Diego, CA (US)

(73) Assignees: Illumina Inc., CA (GB); Illumina Cambridge Limited, Cambridge (GB)

( * ) Notice: Subject to any disclaimer, the term of this patent is extended or adjusted under 35 U.S.C. 154(b) by 0 days.

(21) Appl. No.: 18/233,276

(22) Filed: Aug. 11, 2023

(65) Prior Publication Data

US 2023/0391997 A1 Dec. 7, 2023

Related U.S. Application Data

(63) Continuation of application No. 16/721,451, filed on Dec. 19, 2019, now Pat. No. 11,787,930.

(60) Provisional application No. 62/792,250, filed on Jan. 14, 2019.

(51) Int. Cl.
| | |
|---|---|
| *C08L 33/08* | (2006.01) |
| *C08L 33/26* | (2006.01) |
| *C12Q 1/6853* | (2018.01) |
| *C12Q 1/6869* | (2018.01) |

(52) U.S. Cl.
CPC .............. *C08L 33/08* (2013.01); *C08L 33/26* (2013.01); *C12Q 1/6853* (2013.01); *C12Q 1/6869* (2013.01)

(58) Field of Classification Search
CPC .......... C08L 33/08; C08L 33/26; C08L 33/10; C08L 33/12; C08L 33/04; C08L 33/062; C12Q 1/6853; C12Q 1/6869
See application file for complete search history.

(56) References Cited

U.S. PATENT DOCUMENTS

| | | |
|---|---|---|
| 5,444,139 A | 8/1995 | Valpey, III et al. |
| 7,375,404 B2 | 5/2008 | Park et al. |
| 9,012,022 B2 | 4/2015 | George et al. |
| 9,453,258 B2 | 9/2016 | Kain et al. |
| 9,815,916 B2 | 11/2017 | Brown et al. |
| 10,208,142 B2 | 2/2019 | Brown et al. |
| 2012/0150006 A1 | 6/2012 | Lavanant et al. |
| 2014/0079923 A1 | 3/2014 | George et al. |
| 2016/0122816 A1 | 5/2016 | Brown et al. |
| 2017/0007977 A1 | 1/2017 | Mastroianni et al. |
| 2018/0155469 A1 | 6/2018 | Brown et al. |
| 2018/0207920 A1 | 7/2018 | Venkatesan et al. |

FOREIGN PATENT DOCUMENTS

| | | |
|---|---|---|
| CN | 102040707 A | 5/2011 |
| CN | 103483498 A | 1/2014 |
| CN | 104508060 A | 4/2015 |
| CN | 107108822 A | 8/2017 |
| JP | 2006519979 A | 8/2006 |
| JP | 2007513260 A | 5/2007 |
| JP | 2012201634 A | 10/2012 |
| WO | 2004081624 A1 | 9/2004 |
| WO | 2005038132 A2 | 4/2005 |
| WO | 2013184796 A1 | 12/2013 |
| WO | 2014022749 A1 | 2/2014 |
| WO | 2016066586 A1 | 5/2016 |
| WO | 2017161051 A1 | 9/2017 |
| WO | 2018119057 A1 | 6/2018 |
| WO | 2018213627 A1 | 11/2018 |

OTHER PUBLICATIONS

Sallacan et al., "Imprinting of nucleotide and monosaccharide recognition sites in acrylamidephenylboronic acid-acrylamide copolymer membranes associated with electronic transducers", Analytical Chemistry, vol. 74, No. 3, pp. 702-712, doi: 10.1021/ac0109873, Feb. 1, 2002.

Chaterji, S., et al., "Smart Polymeric Gels: Redefining the Limits of Biomedical Devices", Prog Polym Sci., Author Manuscript; 58 pages, Aug. 1, 2008.

Yang, et al., "Zwitterionic polymer modification of polyamide reverse-osmosis membranes via surface amination and atom transfer radical polymerization for anti-biofouling", Journal of Membrane Science, 550, 332-339, Mar. 5, 2018.

Amaral et al., "Transiently malleable multi-healable hydrogel nanocomposites based on responsive boronic acid copolymers", Polymer Chemistry, vol. 9, No. 4, pp. 525-537, doi:10.1039/c7py01202k, Dec. 21, 2018.

Zhang et al., "pH- and Glucose-Responsive Core-Shell Hybrid Nanoparticles with Controllable Metal-Enhanced Fluorescence Effects", ACS Applied Materials & Interfaces, Feb. 10, 2012, vol. 4, Issue 3, pp. 1747-1751, 2012.

*Primary Examiner* — Jezia Riley
(74) *Attorney, Agent, or Firm* — Dierker & Kavanaugh, P.C.

(57) ABSTRACT

A flow cell includes a support and a heteropolymer attached to the support. The heteropolymer includes an acrylamide monomer including an attachment group to react with a functional group attached to a primer, and a monomer including a stimuli-responsive functional group. The monomer including the stimuli-responsive functional group may be pH-responsive, temperature-responsive, saccharide-responsive, nucleophile-responsive, and/or salt-responsive.

16 Claims, 5 Drawing Sheets

TO FIG. 1E        TO FIG. 1G

FROM FIG. 1D

FLOW CELL INCLUDING A HETEROPOLYMER

CROSS-REFERENCE TO RELATED APPLICATION

This application is a continuation of U.S. Ser. No. 16/721,451, filed Dec. 19, 2019, which itself claims the benefit of U.S. Provisional Application Ser. No. 62/792,250, filed Jan. 14, 2019; the content of each of which is incorporated by reference herein in its entirety.

BACKGROUND

Biological arrays are among a wide range of tools used to detect and analyze molecules, including deoxyribonucleic acid (DNA) and ribonucleic acid (RNA). In these applications, the arrays are engineered to include probes for nucleotide sequences present in genes of humans and other organisms. In certain applications, for example, individual DNA and RNA probes may be attached at locations in a geometric grid (or randomly) on an array support. A test sample, e.g., from a person or organism, may be exposed to the grid, such that complementary fragments hybridize to the probes at the individual sites in the array. The array can then be examined by scanning specific frequencies of light over the sites to identify which fragments are present in the sample, by fluorescence of the sites at which the fragments hybridized.

Biological arrays may be used for genetic sequencing. In general, genetic sequencing involves determining the order of nucleotides or nucleic acids in a length of genetic material, such as a fragment of DNA or RNA. Increasingly longer sequences of base pairs are being analyzed, and the resulting sequence information may be used in various bioinformatics methods to logically fit fragments together so as to reliably determine the sequence of extensive lengths of genetic material from which the fragments were derived. Automated, computer-based examination of characteristic fragments have been developed, and have been used in genome mapping, identification of genes and their function, evaluation of risks of certain conditions and disease states, and so forth. Beyond these applications, biological arrays may be used for the detection and evaluation of a wide range of molecules, families of molecules, genetic expression levels, single nucleotide polymorphisms, and genotyping.

SUMMARY

One aspect disclosed herein is a switchable heteropolymer comprising: a plurality of monomers comprising a stimuli-responsive functional group, wherein the stimuli-responsive functional group is selected from the group consisting of a pH-responsive functional group, a temperature-responsive functional group, a saccharide-responsive functional group, a nucleophile-responsive functional group, and a salt-responsive functional group.

The stimuli-responsive functional group is capable of undergoing modification when exposed to a predetermined stimulus, wherein the modification changes the polarity and/or conformation of the switchable heteropolymer.

In some aspects, the switchable heteropolymer further comprises a primer grafted thereto.

In some aspects, the stimuli-responsive functional group is not an azido group.

In some aspects, the switchable heteropolymer comprises two or more different stimuli-responsive monomers that are responsive to the same or different stimuli.

In some aspects, the switchable heteropolymer is a copolymer comprising a plurality of acrylamide monomers optionally comprising an azido group. In one of these aspects, the acrylamide monomer is an azido acetamido pentyl acrylamide monomer or is a combination of the azido acetamido pentyl acrylamide monomer and a second acrylamide monomer.

In some aspects, the switchable heteropolymer comprises sugar monomers optionally comprising an azido group.

In some aspects, the pH-responsive functional group is selected from the group consisting of a hydroxyl, 1,2-diol, 1,3-diol protected as an acetal, hemiacetal, or ketal, a tert-butyloxycarbonylamino group, a 9H-fluoren-9-yl-methoxycarbonylamino group, an amino group, a carboxylate group, a carboxylic acid group, a sulfonate group, and a sulfonic acid group.

In other aspects, the saccharide-responsive functional group comprises a boronic acid group.

In still other aspects, the nucleophile-responsive functional group has the following structure:

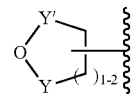

wherein: (a) Y is $SO_2$ and Y' is $CH_2$; or (b) Y and Y' are both C(O).

In yet further aspects, the salt-responsive functional group is a zwitterionic functional group exhibiting antipolyelectrolyte behavior.

In some aspects, the temperature-responsive group includes a heat-sensitive hydroxyl or amino protecting group.

It is to be understood that any features of the switchable heteropolymer disclosed herein may be combined together in any desirable manner and/or configuration.

Another aspect disclosed herein is a method of making a switchable heteropolymer comprising copolymerizing a plurality of monomers comprising a stimuli-responsive functional group with a plurality of a second monomer.

In some aspects, the second monomer is a sugar monomer or an acrylamide monomer comprising an azido group. In some aspects, the acrylamide monomer comprises an azido group. In some aspects, the acrylamide monomer is an azido acetamido pentyl acrylamide monomer or is a combination of the azido acetamido pentyl acrylamide monomer and a second acrylamide monomer.

It is to be understood that any features of this method may be combined together in any desirable manner. Moreover, it is to be understood that any combination of features of the method and/or of the switchable heteropolymer may be used together, and/or combined with any of the examples disclosed herein.

Another aspect disclosed herein is a flow cell comprising a support and a switchable heteropolymer attached to the support. Any of the switchable heteropolymers disclosed herein may be used. In some aspects, the flow cell further comprises a primer grafted to the switchable heteropolymer.

It is to be understood that any features of this flow cell may be combined together in any desirable manner. Moreover, it is to be understood that any combination of features of the flow cell and/or of the method and/or of the switchable heteropolymer may be used together, and/or combined with any of the examples disclosed herein.

Still another aspect disclosed herein is a method of making a flow cell, comprising contacting the switchable heteropolymer with at least a portion of a flow cell support, thereby attaching the switchable heteropolymer to the flow cell support.

In some aspects, the method comprises grafting a primer to the switchable heteropolymer attached to the support.

In other aspects, the method comprises exposing the switchable heteropolymer attached to the flow cell support to the predetermined stimulus. In some aspects, the method further comprises, after the exposing, performing a sequencing operation on the flow cell.

It is to be understood that any features of this method may be combined together in any desirable manner. Moreover, it is to be understood that any combination of features of the flow cell and/or any of the methods and/or of the switchable heteropolymer may be used together, and/or combined with any of the examples disclosed herein.

Still another aspect is a method of sequencing comprising: grafting a primer to a switchable heteropolymer on a flow cell support; exposing a switchable heteropolymer on a flow cell support to a predetermined stimulus, thereby causing a change in the polarity and/or conformation of the switchable heteropolymer; hybridizing the nucleic acid template to the primer on the flow cell support; amplifying the nucleic acid template on the flow cell support to produce an amplified template; and detecting a signal when a labeled nucleotide associates with a complementary nucleotide in the amplified template.

It is to be understood that any features of this method may be combined together in any desirable manner. Moreover, it is to be understood that any combination of features of the flow cell and/or any of the methods and/or of the switchable heteropolymer may be used together in any desirable manner, and/or combined with any of the examples disclosed herein.

Yet another aspect disclosed herein is a heteropolymer, comprising a monomer comprising an attachment group to react with a functional group attached to a primer, and a monomer comprising a stimuli-responsive functional group, wherein the monomer comprising the stimuli-responsive functional group is selected from the group consisting of: an acrylamide monomer including a terminal pH-responsive functional group; a vinyl or acrylate monomer including a terminal pH-responsive functional group selected from the group consisting of a hydroxyl with an acid-labile protecting group, a hydroxyl with a base-labile protecting group, an amino with an acid-labile protecting group, an amino with a base-labile protecting group, a sulfonate group and a sulfonic acid group; a temperature-responsive N-substituted acrylamide; an acrylamide, acrylate, or vinyl monomer including a terminal saccharide-responsive functional group; an acrylamide, acrylate, or vinyl monomer including a terminal nucleophile-responsive functional group; and an acrylamide, acrylate, or vinyl monomer including a terminal salt-responsive functional group.

In some aspects, the monomer comprising the stimuli-responsive functional group is to undergo modification when exposed to a predetermined stimulus, wherein the modification changes the polarity and/or conformation of the switchable heteropolymer.

Some aspects of this heteropolymer further comprise the primer grafted to the attachment group.

In some aspects, the attachment group is selected from the group consisting of an azido group, an alkenyl group, an alkynyl group, an aldehyde group, a hydrazone group, a hydrazine group, a tetrazole group, a tetrazine group, and a thiol group.

In other aspects, the attachment group of the acrylamide monomer comprises an azido group. In some examples, acrylamide monomer is an azido acetamido pentyl acrylamide monomer. In some examples, the heteropolymer further comprises a second acrylamide monomer.

In some aspects, the monomer comprising the stimuli-responsive functional group is the acrylamide monomer including the terminal pH-responsive functional group; and the terminal pH-responsive functional group is selected from the group consisting of a hydroxyl, 1,2-diol, 1,3-diol protected as an acetal, hemiacetal, or ketal, a tert-butyloxycarbonylamino group, a 9H-fluoren-9-ylmethoxycarbonylamino group, an amino group, a carboxylate group, a carboxylic acid group, a sulfonate group, and a sulfonic acid group.

In other aspects, the monomer comprising the stimuli-responsive functional group is the acrylamide, acrylate, or vinyl monomer including the terminal saccharide-responsive functional group; and the terminal saccharide-responsive functional group comprises a boronic acid group. In one example, the monomer comprising the stimuli-responsive functional group is 3-(acrylamido)phenylboronic acid.

In some aspects, the monomer comprising the stimuli-responsive functional group is the acrylamide, acrylate, or vinyl monomer including the terminal nucleophile-responsive functional group; and the terminal nucleophile-responsive functional group has the following structure:

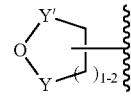

wherein: (a) Y is $SO_2$ and Y' is $CH_2$; or (b) Y and Y' are both C(O).

In other aspects, the monomer comprising the stimuli-responsive functional group is the acrylamide, acrylate, or vinyl monomer including the terminal salt-responsive functional group; and the salt-responsive functional group is a zwitterionic functional group exhibiting antipolyelectrolyte behavior. In an example, the monomer comprising the stimuli-responsive functional group has one of the following structures:

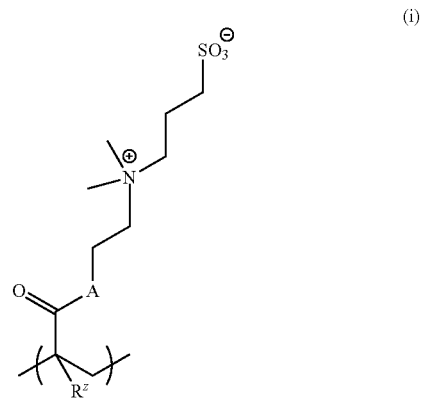

(i)

wherein A is O or NH and $R^z$ is H or $C_{1-4}$alkyl; or

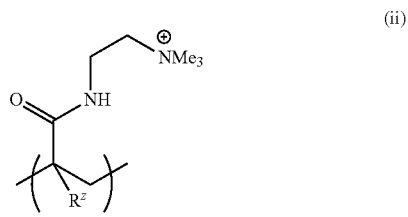

(ii)

wherein $R^z$ is H or $C_{1-4}$alkyl.

In some aspects, the monomer comprising the stimuli-responsive functional group is the temperature-responsive N-substituted acrylamide; and the temperature-responsive-substituted acrylamide includes a heat-sensitive hydroxyl or amino protecting group.

In some aspects, the monomer comprising the stimuli-responsive functional group is the temperature-responsive N-substituted acrylamide; and the temperature-responsive N-substituted acrylamide is N-isopropylacrylamide.

It is to be understood that any features of this heteropolymer may be combined together in any desirable manner. Moreover, it is to be understood that any combination of features of the heteropolymer and/or of the flow cell and/or any of the methods may be used together in any desirable manner, and/or combined with any of the examples disclosed herein.

Another aspect disclosed herein is a heteropolymer having a structure:

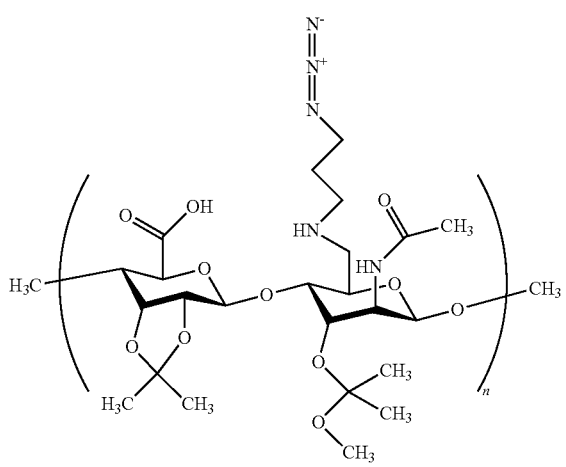

wherein n ranges from 10 to 500.

It is to be understood that any combination of features of this heteropolymer and/or of the flow cell and/or any of the methods may be used together in any desirable manner, and/or combined with any of the examples disclosed herein.

Still another aspect disclosed herein is a method of making a heteropolymer comprising selecting the monomer comprising a stimuli-responsive functional group from the group consisting of an acrylamide monomer including a terminal pH-responsive functional group; a vinyl or acrylate monomer including a terminal pH-responsive functional group selected from the group consisting of a hydroxyl with an acid-labile protecting group, a hydroxyl with a base-labile protecting group, an amino with an acid-labile protecting group, an amino with a base-labile protecting group, a sulfonate group and a sulfonic acid group; a temperature-responsive N-substituted acrylamide; an acrylamide, acrylate, or vinyl monomer including a terminal saccharide-responsive functional group; an acrylamide, acrylate, or vinyl monomer including a terminal nucleophile-responsive functional group; and an acrylamide, acrylate, or vinyl monomer including a terminal salt-responsive functional group; and copolymerizing the the monomer comprising the stimuli-responsive functional group with an acrylamide monomer comprising an attachment group to react with a functional group attached to a primer.

In some aspects, the acrylamide monomer comprising the attachment group is an azido acetamido pentyl acrylamide monomer.

Some aspects of this method further comprise copolymerizing the monomer comprising a stimuli-responsive functional group and acrylamide monomer comprising the attachment group with a second acrylamide monomer.

It is to be understood that any combination of features of this method, and/or of the flow cell and/or any of the heteropolymers may be used together in any desirable manner, and/or combined with any of the examples disclosed herein.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Figure 1A:
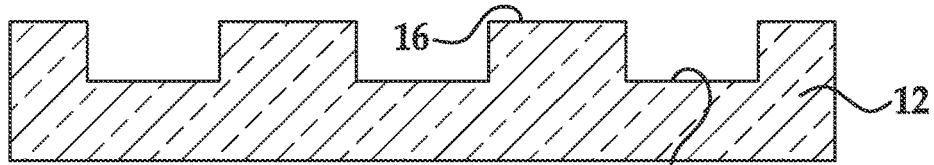
FIGS. 1A through 1D, along with FIGS. 1E and 1F, or along with FIGS. 1G and 1H, are schematic cross-sectional views depicting respective examples of the method disclosed herein.

The singular forms "a", "an", and "the" include plural referents unless the context clearly dictates otherwise.

The terms comprising, including, containing and various forms of these terms are synonymous with each other and are meant to be equally broad.

The terms top, bottom, lower, upper, on, and related terms, are used herein to describe the flow cell and/or the various components of the flow cell. It is to be understood that these directional terms are not meant to imply a specific orientation but are used to designate relative orientation between components. The use of directional terms should not be interpreted to limit the examples disclosed herein to any specific orientation(s).

As used herein, "acetal group" refers to a functional group with the following connectivity $R_2C(OR')_2$, where the R groups and R' groups are each organic fragments. Acetal groups include acetals, ketals, hemiacetals, and hemiketals. In an acetal, one R group is H. In some aspects, R' is $C_{1-4}$alkyl, or the two R' groups taken together form a $C_{2-4}$alkylene. An acetal protecting group can be used to protect a hydroxyl group, a 1,2-diol, or a 1,3-diol.

An "acrylate group" includes the salts, esters, and conjugate bases of acrylic acid and its derivatives (e.g., methacrylic acid). The acrylate ion has the molecular formula $CH_2=CHCOO^-$.

An "acrylamide monomer" is a monomer with the structure

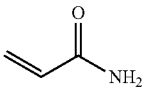

or a substituted analog thereof (e.g., methacrylamide or N-isopropylacrylamide). An example of a monomer including an acrylamide group and an azido group is azido acetamido pentyl acrylamide:

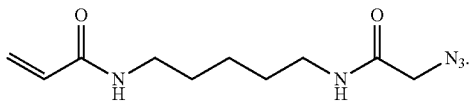 [SMILES: C=CC(=O)NCCCCCNC(=O)CN=[N+]=[N-]]

As used herein, "alkyl" refers to a straight or branched hydrocarbon chain that is fully saturated (i.e., contains no double or triple bonds). The alkyl group may have 1 to 20 carbon atoms. Example alkyl groups include methyl, ethyl, propyl, isopropyl, butyl, isobutyl, tertiary butyl, pentyl, hexyl, and the like. As an example, the designation "C1-4 alkyl" indicates that there are one to four carbon atoms in the alkyl chain, i.e., the alkyl chain is selected from the group consisting of methyl, ethyl, propyl, iso-propyl, n-butyl, isobutyl, sec-butyl, and t-butyl.

As used herein, "alkenyl" refers to a straight or branched hydrocarbon chain containing one or more double bonds. The alkenyl group may have 2 to 20 carbon atoms. Example alkenyl groups include ethenyl, propenyl, butenyl, pentenyl, hexenyl, and the like.

As used herein, "alkyne" or "alkynyl" refers to a straight or branched hydrocarbon chain containing one or more triple bonds. The alkynyl group may have 2 to 20 carbon atoms.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms. Examples of aryl groups include phenyl, naphthyl, azulenyl, and anthracenyl.

As used herein, the term "attached" refers to the state of two things being joined, fastened, adhered, connected, or bound to each other, either covalently or non-covalently (e.g., by hydrogen bonds, ionic bonds, van der Waals forces, hydrophilic interactions and hydrophobic interactions). For example, a nucleic acid can be attached to a functionalized polymer by a covalent or non-covalent bond.

An "azide" or "azido" functional group refers to $-N_3$.

As used herein, the "bonding region" refers to an area on a substrate that is to be bonded to another material, which may be, as examples, a spacer layer, a lid, another substrate, etc., or combinations thereof (e.g., a spacer layer and a lid). The bond that is formed at the bonding region may be a chemical bond (as described above), or a mechanical bond (e.g., using a fastener, etc.).

A "tert-butyloxycarbonyl group" (Boc) refers to a

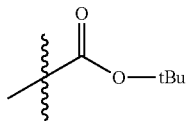

group. A "butyloxycarbonyloxy group" refers to a $-OCO_2tBu$ group.

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation, provided that at least one ring in a ring system is not aromatic. Thus, carbocyclyls include cycloalkyls, cycloalkenyls, and cycloalkynyls. The carbocyclyl group may have 3 to 20 carbon atoms. Examples of carbocyclyl rings include cyclopropyl, cyclobutyl, cyclopentyl, cyclohexyl, cyclohexenyl, 2,3-dihydro-indene, bicyclo[2.2.2]octanyl, adamantyl, and spiro[4.4]nonanyl.

As used herein, the term "carboxylic acid" or "carboxyl" refers to $-COOH$.

As used herein, "cycloalkylene" means a fully saturated carbocyclyl ring or ring system that is attached to the rest of the molecule via two points of attachment.

As used herein, "cycloalkenyl" or "cycloalkene" means a carbocyclyl ring or ring system having at least one double bond, wherein no ring in the ring system is aromatic. Examples include cyclohexenyl or cyclohexene and norbornenyl or norbornene. Also as used herein, "heterocycloalkenyl" or "heterocycloalkene" means a carbocyclyl ring or ring system with at least one heteroatom in ring backbone, having at least one double bond, wherein no ring in the ring system is aromatic.

As used herein, "cycloalkynyl" or "cycloalkyne" means a carbocyclyl ring or ring system having at least one triple bond, wherein no ring in the ring system is aromatic. An example is cyclooctyne. Another example is bicyclononyne. Also as used herein, "heterocycloalkynyl" or "heterocycloalkyne" means a carbocyclyl ring or ring system with at least one heteroatom in ring backbone, having at least one triple bond, wherein no ring in the ring system is aromatic.

The term "depositing," as used herein, refers to any suitable application technique, which may be manual or automated, and results in modification of the surface properties. Generally, depositing may be performed using vapor deposition techniques, coating techniques, grafting techniques, or the like. Some specific examples include chemical vapor deposition (CVD), spray coating (e.g., ultrasonic spray coating), spin coating, dunk or dip coating, doctor blade coating, puddle dispensing, flow through coating, aerosol printing, screen printing, microcontact printing, inkjet printing, or the like.

As used herein, the term "depression" refers to a discrete concave feature in a patterned support having a surface opening that is completely surrounded by interstitial region(s) of the patterned support surface. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc. As an example, the depression can be a well. Also as used herein, a "functionalized depression" refers to the discrete concave feature where the polymer disclosed herein and primer(s) are attached.

The term "each," when used in reference to a collection of items, is intended to identify an individual item in the collection but does not necessarily refer to every item in the collection. Exceptions can occur if explicit disclosure or context clearly dictates otherwise.

As used herein, the term "flow cell" is intended to mean a vessel having a chamber (i.e., flow channel) where a reaction can be carried out, an inlet for delivering reagent(s) to the chamber, and an outlet for removing reagent(s) from the chamber. In some examples, the chamber enables the detection of a reaction or signal that occurs in the chamber. For example, the chamber can include one or more transparent surfaces allowing for the optical detection of arrays, optically labeled molecules, or the like, in the chamber.

As used herein, a "flow channel" or "flow channel region" may be an area defined between two bonded components, which can selectively receive a liquid sample. In some examples, the flow channel may be defined between a patterned support and a lid, and thus may be in fluid communication with one or more depressions defined in the patterned support. In other examples, the flow channel may be defined between a non-patterned support and a lid.

A "fluorenylmethyloxycarbonyl" group (Fmoc) is a base-labile protecting group having a structure

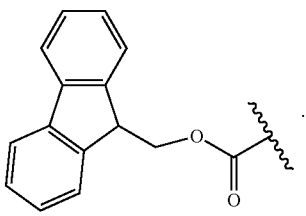 [SMILES: *C(=O)OCC1c2ccccc2-c2ccccc21]

As used herein, "heteroaryl" refers to an aromatic ring or ring system (e.g., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members.

As used herein, "heterocyclyl" means a non-aromatic cyclic ring or ring system containing at least one heteroatom in the ring backbone. Heterocyclyls may be joined together in a fused, bridged, or spiro-connected fashion. Heterocyclyls may have any degree of saturation provided that at least one ring in the ring system is not aromatic. In the ring system, the heteroatom(s) may be present in either a non-aromatic or aromatic ring. The heterocyclyl group may have 3 to 20 ring members (i.e., the number of atoms making up the ring backbone, including carbon atoms and heteroatoms). In some examples, the heteroatom(s) are O, N, or S.

The term "hydrazine" or "hydrazinyl" as used herein refers to an optionally substituted —NHNH$_2$ group.

As used herein, the term "hydrazone" or "hydrazonyl" as used herein refers to a

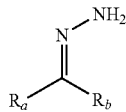

group in which R$_a$ and R$_b$ are each independently selected from hydrogen, C1-6 alkyl, C2-6 alkenyl, C2-6 alkynyl, C3-7 carbocyclyl, C6-10 aryl, 5-10 membered heteroaryl, and 5-10 membered heterocyclyl, as defined herein.

As used herein, "hydroxy" or "hydroxyl" refers to an —OH group.

As used herein, the term "interstitial region" refers to an area in a support or on a surface that separates depressions. For example, an interstitial region can separate one feature of an array from another feature of the array. The two features that are separated from each other can be discrete, i.e., lacking physical contact with each other. In another example, an interstitial region can separate a first portion of a feature from a second portion of a feature. In many examples, the interstitial region is continuous whereas the features are discrete, for example, as is the case for a plurality of wells defined in an otherwise continuous surface. The separation provided by an interstitial region can be partial or full separation. Interstitial regions may have a surface material that differs from the surface material of the features defined in the surface. For example, features of an array can have an amount or concentration of the coating layer and primer(s) that exceeds the amount or concentration present at the interstitial regions. In some examples, the coating layer and primer(s) may not be present at the interstitial regions.

As used herein, a "nucleotide" includes a nitrogen-containing heterocyclic base, a sugar, and one or more phosphate groups. Nucleotides are monomeric units of a nucleic acid sequence. In RNA, the sugar is a ribose, and in DNA, the sugar is a deoxyribose, i.e. a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, "plasma ashing" refers to a process of removing organic matter from a support by an oxygen plasma. The products that result from plasma ashing may be removed with a vacuum pump/system. Plasma ashing can activate the support by introducing reactive hydroxyl groups.

The "heteropolymer" or "heteropolymer coating layer" referred to herein is intended to mean a large molecule of at least two different repeating subunits (monomers), wherein one of the repeating subunits (monomers) includes a stimuli-responsive functional group.

As used herein, the "primer" is defined as a single stranded nucleic acid sequence (e.g., single strand DNA or single strand RNA) that serves as a starting point for DNA or RNA synthesis. The 5' terminus of the primer may be modified to allow a coupling reaction with the functionalized polymer layer. The primer length can be any number of bases long and can include a variety of non-natural nucleotides. In an example, the primer is a short strand, ranging from 20 to 40 bases.

As used herein, the terms "silane" and "silane derivative" refer to an organic or inorganic compound containing one or more silicon atoms. An example of an inorganic silane compound is SiH$_4$, or halogenated SiH$_4$ where hydrogen is replaced by one or more halogen atoms. An example of an organic silane compound is X—R$^B$—Si(OR$^C$)$_3$, wherein R—Si is an organic linker, and wherein X is a functional group, such as amino, vinyl, methacrylate, epoxy, sulfur, alkyl, alkenyl, or alkynyl; $R_B$ is a spacer, for example —$(CH_2)_n$—, wherein n is 0 to 1000; $R^C$ is selected from hydrogen, optionally substituted alkyl, optionally substituted alkenyl, optionally substituted alkynyl, optionally substituted carbocyclyl, optionally substituted aryl, optionally substituted 5-10 membered heteroaryl, and optionally substituted 5-10 membered heterocyclyl, as defined herein. As used herein, the terms "silane" and "silane derivative" can include mixtures of different silane and/or silane derivative compounds.

A "spacer layer," as used herein refers to a material that bonds two components together. In some examples, the spacer layer can be a radiation-absorbing material that aids in bonding or can be put into contact with a radiation-absorbing material that aids in bonding.

A "stimuli-responsive functional group," as used herein, refers to a moiety of atoms and/or bonds within the polymer that can change its state in response to a stimulus. The stimuli-responsive functional group may be pH-responsive, temperature-responsive, saccharide-responsive, nucleophile-responsive, or salt-responsive. Specific examples of each stimuli-responsive functional group will be described further below.

The term flow cell "support" or "substrate" refers to a support or substrate upon which surface chemistry may be added. The term "patterned substrate" refers to a support in which or on which depressions are defined. The term "non-patterned substrate" refers to a substantially planar support. The substrate may also be referred to herein as a "support," "patterned support," or "non-patterned support." The support may be a wafer, a panel, a rectangular sheet, a die, or any other suitable configuration. The support is generally rigid and is insoluble in an aqueous liquid. The support may be inert to a chemistry that is used to modify the depressions. For example, a support can be inert to chemistry used to form the polymer coating layer, to attach the primer(s) to the polymer coating layer, etc. Examples of suitable supports include epoxy siloxane, glass and modified or functionalized glass, polyhedral oligomeric silsequioxanes (POSS) and derivatives thereof, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon, ceramics/ceramic oxides, silica, fused silica, or silica-based materials, aluminum silicate, silicon and modified silicon (e.g., boron doped p+ silicon), silicon nitride ($Si_3N_4$), silicon oxide ($SiO_2$), tantalum pentoxide ($TaO_5$) or other tantalum oxide(s) ($TaO_x$), hafnium oxide ($HaO_2$), carbon, metals, inorganic glasses, or the like. The support may also be glass or silicon or a silicon-based polymer such as a POSS material, optionally with a coating layer of tantalum oxide or another ceramic oxide at the surface.

The term "surface chemistry," as used herein, refers to chemically and/or biologically active component(s) that are incorporated into the channel of the flow cell. Examples of the surface chemistry disclosed herein include the polymer coating layer attached to at least a portion of a surface of the support and the primer attached to at least a portion of the polymer coating layer.

A "thiol" functional group refers to —SH.

As used herein, the terms "tetrazine" and "tetrazinyl" refer to six-membered heteroaryl group comprising four nitrogen atoms. Tetrazine can be optionally substituted.

"Tetrazole," as used herein, refer to five-membered heterocyclic group including four nitrogen atoms. Tetrazole can be optionally substituted.

Examples of the flow cell disclosed herein include a support, a polymer attached to the support, and a primer grafted to the polymer. Examples of the flow cells are shown in FIGS. 1F, 1H, and 3D, and will be described further herein. Various examples of the polymer that is attached to the flow cell support will now be described.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range, as if such ranges, values or sub-ranges were explicitly recited herein. For example, a range from about 400 nm to about 1 μm (1000 nm), should be interpreted to include not only the explicitly recited limits of from about 400 nm to about 1 μm, but also to include individual values, such as about 708 nm, about 945.5 nm, etc., and sub-ranges, such as from about 425 nm to about 825 nm, from about 550 nm to about 940 nm, etc. Furthermore, when "about" and/or "substantially" are/is utilized to describe a value, they are meant to encompass minor variations (up to +/−10%) from the stated value.

The heteropolymers described herein comprise a stimuli-responsive functional group that is capable of undergoing modification when exposed to a predetermined stimulus, wherein the modification changes the polarity and/or conformation of the heteropolymer. Therefore, examples of the heteropolymer disclosed herein may be switchable. The switchable heteropolymers can transition from a starting state to a second, switched state upon exposure to the particular stimulus. Examples of switches include changes to polarity such as hydrophobic to hydrophilic, increasing hydrophilicity, hydrophilic to hydrophobic, increasing hydrophobicity, neutral to charged, charged to neutral, anionic to neutral, cationic to neutral, neutral to anionic, neutral to cationic, and neutral to neutral with increased hydrophilicity. Examples of switches also include conformational changes such as swelling, collapsed state to extended state, extended state to collapsed state (e.g., with antipolyelectrolyte behavior), and coil-globule formation. A given stimuli-responsive group may impart more than one switching effect. In some aspects, the switch is irreversible, and in other examples, the switch is reversible under different chemical or thermal conditions.

The stimuli-responsive functional group exhibits a starting state when the switchable heteropolymer is applied to the flow cell support. In some aspects, the starting state is compatible with the hydrophobic nature of a flow cell support, and this compatibility eases manufacture and handling of the flow cell. For example, the starting state (e.g., hydrophobic) may improve adhesion to and coating uniformity of the heteropolymer to a hydrophobic flow cell support, while the switched state may be more compatible with flow cell uses such as sequencing operations.

Thus, in some aspects, the switched state may be a solution conformation that provides improved performance in some applications, including sequencing operations. Prior to a sequencing operation, the stimuli-responsive polymers disclosed herein may be exposed to the predetermined stimulus. Upon exposure to the stimulus, the switchable heteropolymer changes polarity and/or conformation due to the effects of the predetermined stimulus on the stimuli-responsive functional group. The heteropolymer in the switched state(s) can provide a low-fouling surface that may reduce non-specific adsorption of proteins and that may improve sequencing metrics (e.g., base or $1^{st}$ cycle intensity, quality scores, error rates, etc.).

One of ordinary skill will recognize that any of the heteropolymers described herein may be random, block, linear, and/or branched copolymers comprising two or more recurring monomer units in any order or configuration, and may be linear, cross-linked, or branched, or a combination thereof.

In some examples, the stimuli-responsive functional group is a pH-responsive functional group. In such aspects, the switchable heteropolymer is a copolymer comprising a plurality of monomers comprising a pH-responsive functional group. The plurality of monomers may each have the same pH-responsive functional group or different pH-responsive functional groups that respond to the same pH condition. In some aspects, the heteropolymer is a copolymer with a plurality of acrylamide monomers. A single type of acrylamide monomer may be used, or two or more different acrylamide monomers may be used.

In some aspects, a pH-responsive functional group is converted to a substituent group with increased or decreased polarity (e.g., increased hydrophilicity or increased hydrophobicity) upon exposure to acidic or basic pH conditions. In some aspects, the pH-responsive functional group is neutral and becomes charged upon exposure to the stimulus. In some aspects, the pH-responsive functional group is charged and becomes neutral upon exposure to the stimulus. In some aspects, the pH-responsive functional group is neutral and is converted to a different, neutral, but more polar, group upon exposure to the stimulus.

In some aspects, a pH-responsive functional group is a hydroxyl with an acid-labile protecting group (switches to a more hydrophilic free hydroxyl upon exposure to acidic/low pH conditions), a hydroxyl with a base-labile protecting group (switches to a more hydrophilic free hydroxyl upon exposure to basic/high pH conditions), an amino with an acid-labile protecting group (switches to a more hydrophilic free amino group upon exposure to acidic/low pH conditions), an amino with a base-labile protecting group (switches to a more hydrophilic free amino group upon exposure to basic/high pH conditions), an amino group (switches to an ammonium ion under acidic/low pH conditions), a carboxylate ($—CO_2^-$) group (switches to a neutral carboxylic acid upon exposure to acidic/low pH conditions, a carboxylic acid group (switches to a charged and more hydrophilic carboxylate upon exposure to basic/high pH conditions), a sulfonate ($—SO_3^-$) group (switches to a neutral sulfonic acid upon exposure to acidic/low pH conditions), or a sulfonic acid group (switches to a charged and more hydrophilic sulfonate upon exposure to basic/high pH conditions).

An exemplary switchable heteropolymer comprises a monomer of the following structure:

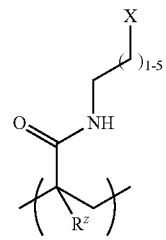

where:
X is a pH-responsive functional group selected from the group consisting of —O—PG, —NH—PG, —NR$^a$R$^b$, —SO$_3$H, —SO$_3$, —CO$_2$H, and —CO$_2$;

PG is an acid- or base-labile protecting group (e.g., Boc, Fmoc, or acetal);

R$^a$ and R$^b$ are each independently H or C$_{1-4}$alkyl; and each R$^z$ is independently H or C$_{1-4}$alkyl.

In some aspects, X is —O-Boc, —NHBoc, —NHFmoc, —NH$_2$, —NHCH$_3$, or —N(CH$_3$)$_2$. In some aspects, X is SO$_3$H, —SO$_3^-$, —CO$_2$H, or —CO$_2^-$. In some aspects, R$^a$ and R$^b$ are both methyl. In some aspects, R$^z$ is H or methyl. In some aspects, the monomer has the structure:

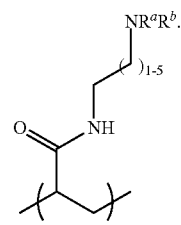

Thus, in some aspects, the pH-responsive functional group is a hydroxyl, 1,2-diol, or 1,3-diol protected as an acetal, hemiacetal, or ketal (switches to a more polar/hydrophilic diol upon exposure to acidic/low pH conditions), a tert-butyloxycarbonylamino group, a 9H-fluoren-9-ylmethoxycarbonylamino group, an amino group, a carboxylate (—CO$_2^-$) group, a carboxylic acid group, a sulfonate (—SO$_3^-$) group, or a sulfonic acid group.

A tert-butoxycarbonylamino group may be in a hydrophobic (or less hydrophilic) state, and when exposed to a low (acidic) pH (e.g., having a pH less than 7), may transition to a hydrophilic state (e.g., an amino group). The tert-butoxycarbonylamino group may be attached to an acrylamide monomer or an acrylate monomer. Examples of the tert-butoxycarbonylamino group containing monomer include N-(tert-butoxycarbonyl-aminoethyl) methacrylamide, N-(tert-butoxycarbonyl-aminopropyl) methacrylamide, and (2-tert-butoxycarbonyl-amino)ethyl methacrylate.

The 9H-fluoren-9-ylmethoxycarbonylamino group may be in a hydrophobic (or less hydrophilic) state, and when exposed to a low (acidic) pH (e.g., having a pH less than 7), may transition to a hydrophilic state (e.g., an amino group). The 9H-fluoren-9-ylmethoxycarbonylamino group may be attached to an acrylamide monomer, or an acrylate monomer, or a vinyl monomer. An example of the 9H-fluoren-9-ylmethoxycarbonyl group containing monomer includes:

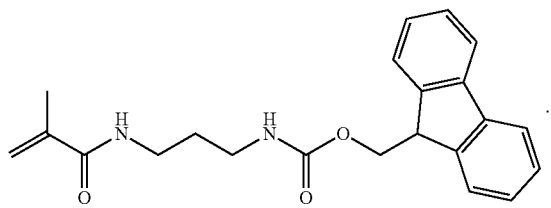 [SMILES: C=C(C)C(=O)NCCCNC(=O)OCC1c2ccccc2-c2ccccc21]

The amino group may be in a neutral state, and when exposed to low (acidic) pH (e.g., having a pH less than 7), may transition to a charged (and more hydrophilic) state (cationic). For example, the amino groups in the synthesized polymer may be protonated, which leads to cationic charges around the polymer backbone. In the synthesized polymer, the amino group may be attached to an acrylamide monomer, or an acrylate monomer, or a vinyl monomer. Examples of an amino group containing monomer include 2-(dimethylamino)ethyl methacrylate, 2-(N,N-dimethylamino)ethyl acrylate, N-[3-(N,N-dimethylamino)propyl] acrylamide, N-[2-(N,N-dimethylamino)ethyl]methacrylamide, and N-[3-(N,N-dimethylamino)propyl]methacrylamide.

An acetal group, when exposed to low (acidic) pH (e.g., pH less than 7), may transition to a more hydrophilic state than its starting state (a hydroxyl or diol). The acetal group may be attached to azide-functionalized hyaluronic acid (HA-$N_3$). HA-$N_3$ has limited solubility in organic solvents, and thus may be converted to its tetrabutylammonium salt using acidic ion exchange resin prior to the acetalation reaction. The acetalation reaction may be performed by reacting, at room temperature, 2-methoxypropene and pyridinium p-toluenesulfonate with the HA-$N_3$ salt solubilized in dimethyl sulfoxide (DMSO).

In some aspects, the switchable heteropolymer further comprises an azido-containing acrylamide monomer. In some aspects, the switchable heteropolymer comprises:

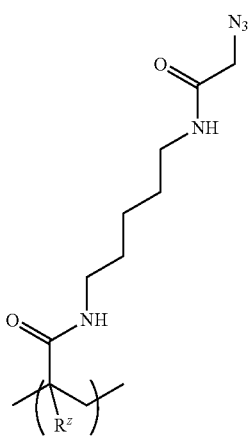

and optionally

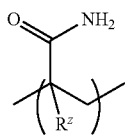

In some aspects, the switchable heteropolymer comprises the structure:

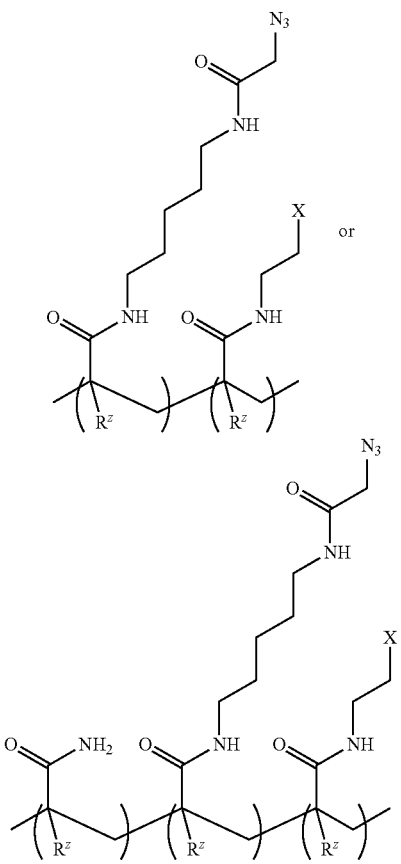

where each $R^z$ is independently H or $C_{1-4}$alkyl. In some examples, X is —O-Boc, —NHBoc, —NHFmoc, —$NH_2$, —$NHCH_3$, or —$N(CH_3)_2$. In some examples, X is —NH-Boc. In some aspects, X is $SO_3H$, —$SO_3^-$, —$CO_2H$, or —$CO_2^-$. In some aspects, $R^a$ and $R^b$ are both methyl. In some aspects, each $R^z$ is independently H or methyl.

In some examples, the switchable heteropolymer comprises two pH-responsive acetal functional groups (such as one ketal group and one hemiketal group) and a carboxylic acid group. An exemplary heteropolymer has the following structure:

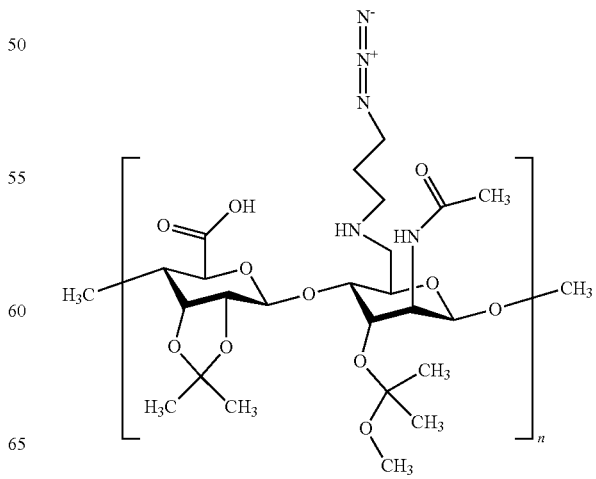

wherein n ranges from 10 to 500. The acid-labile acetal groups protect a plurality of alcohols on the polar dextran backbone of the azido-modified hyaluronic acid (HA-N$_3$), and change the character of the heteropolymer from hydrophilic to hydrophobic. The heteropolymer in its more hydrophobic starting state may be easier to handle and process, allowing the heteropolymer to coat or adhere to the hydrophobic supports disclosed herein (e.g., norbornene-functionalized glass or POSS substrates) more effectively.

In some examples, the stimuli-responsive functional group is a temperature-responsive functional group. In such aspects, the switchable heteropolymer is a copolymer comprising a plurality of monomers comprising a temperature-responsive functional group. The plurality of monomers may each have the same temperature-responsive functional group or different temperature-responsive functional groups that respond to the same temperature condition. In some aspects, the heteropolymer is a copolymer with a plurality of acrylamide monomers. A single type of acrylamide monomer may be used, or two or more different acrylamide monomers may be used.

A temperature-responsive functional group is one that can be converted to a more or less polar functional group or causes conformational change to the polymer due to a temperature change. For example, a temperature-responsive group includes a heat-sensitive hydroxyl or amino protecting group (such as a Boc or Fmoc group) that is removed upon exposure of the heteropolymer to heat (switching from neutral starting state to neutral with increased hydrophilicity). A variety of Boc and Fmoc-protected monomers may be used including acrylic monomers. In another example, a temperature-responsive functional group can cause the polymer to exist in an extended starting state that is neutral and relatively hydrophilic at room temperature and then switch the heteropolymer to a collapsed state that is neutral and relatively hydrophobic at an elevated temperature (such as above 32° C.). This other example is a coil-globule switch, which may be exhibited, for example, by poly(N-isopropylacrylamide). It is to be understood that the primers grafted to this switchable heteropolymers may alter this behavior slightly. In some aspects, this polymeric material undergoes a thermal coil-to-globule transition. In some aspects, the temperature-responsive functional group is part of a polymer that is an ionizable, thermosensitive gel. In some aspects, the monomer comprising the temperature responsive functional group is an N-substituted acrylamide, such as H$_2$C═C(H or methyl)-C(O)NR$^c$R$^d$, where R$^c$ is H and R$^d$ is a branched C$_{3-6}$alkyl. In some aspects, the monomer comprising the temperature-responsive functional group is N-isopropylacrylamide, optionally in a block of poly(N-isopropylacrylamide).

In an example, the heteropolymer comprises a temperature-responsive functional group monomer and an acrylamide monomer. In some examples, the acrylamide monomer is selected from the group consisting of an azido acetamido pentyl acrylamide monomer and a combination of an acrylamide monomer and the azido acetamido pentyl acrylamide monomer as shown above. In some aspects, the switchable heteropolymer further comprises an azido-containing acrylamide monomer. In some aspects, the switchable heteropolymer comprises:

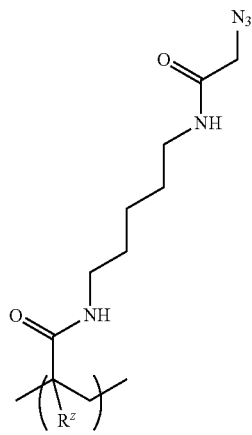

and optionally

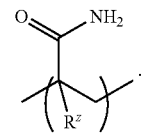

In some aspects, the switchable heteropolymer comprises the structure:

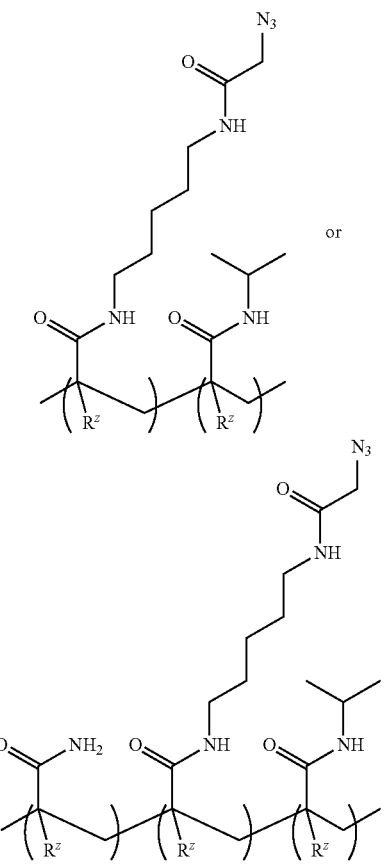

where each R$^z$ is independently H or C$_{1-4}$alkyl.

In another aspect, the stimuli-responsive functional group is a saccharide-responsive functional group, which is a hydrophilic substituent group that reacts with a diol reagent to form an anionic functional group. In some aspects, the diol is an organic diol, or a sugar, or glucose. In some aspects, the saccharide-responsive functional group comprises a boronic acid, such as an alkyl boronic acid or an aryl boronic acid. The boronic acid functional group may be in a charge neutral starting state (and may also be relatively hydrophobic), and when exposed to a saccharide solution, may transition to a negatively charged (anionic) state (that may also be more hydrophilic than the charge neutral state). Boronic acids have the ability to react with saccharides to form boronate esters that undergo reversible swelling due to an influx of water, which may be desirable during sequencing operations.

The boronic acid functional group may be attached to an acrylamide monomer, or an acrylate monomer, or a vinyl monomer. In an example, the monomer comprising the saccharide-responsive functional group has the structure:

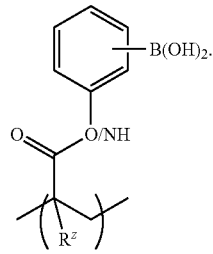

An example of the boronic acid group containing monomer includes 3-(acrylamido)phenylboronic acid. In some aspects, the switchable heteropolymer further comprises an acrylamide monomer. In some aspects, the acrylamide monomer is an azido-containing acrylamide monomer. In some aspects, the switchable heteropolymer comprises:

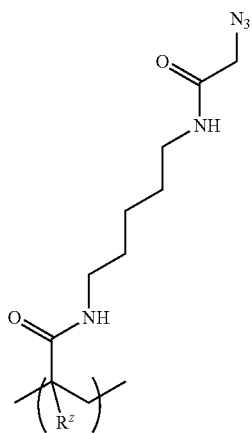

and optionally

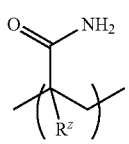

In some aspects, the heteropolymer has a structure:

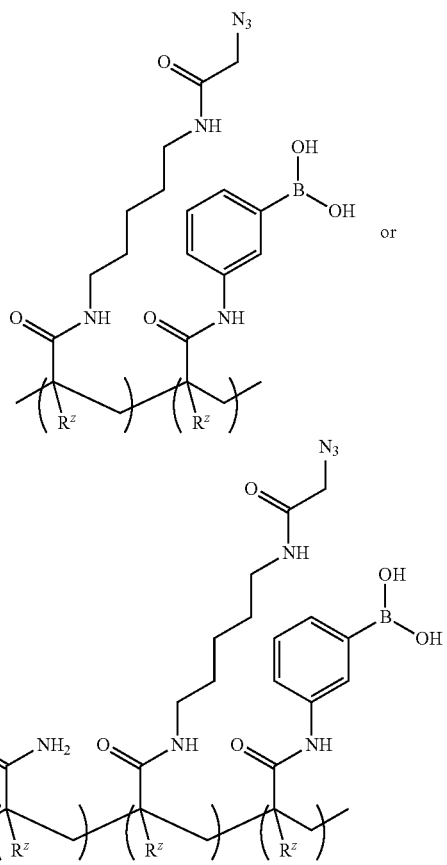

where each $R^z$ is independently H or $C_{1-4}$alkyl.

In some examples, the stimuli-responsive functional group is a nucleophile-responsive functional group. A nucleophile-responsive functional group is a group that is susceptible to attack by a nucleophile to effect a structural change that confers a change in polarity and/or conformation as described herein. In some aspects, the switchable heteropolymer is a copolymer comprising a plurality of monomers comprising a nucleophile-responsive functional group. The plurality of monomers may each have the same nucleophile-responsive functional group or different nucleophile-responsive functional groups that respond to the same nucleophile. In some aspects, the heteropolymer is a copolymer of the monomer comprising a nucleophile-responsive functional group and one or more acrylamide monomers. A single type of acrylamide monomer may be used, or two or more different acrylamide monomers may be used. In some examples, the nucleophile-responsive functional group is a cyclic sulfonate ester (such as a sultone ring) or a cyclic anhydride (such as succinic anhydride) that can undergo a ring-opening reaction upon exposure to a nucleophile, in some cases under basic (high pH) conditions such as pH 9 or greater.

In some aspects, the nucleophile-responsive functional group has the following structure:

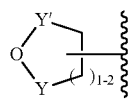

where (a) Y is $SO_2$ and Y' is $CH_2$; or (b) Y and Y' are both C(O). In other aspects, the nucleophile-responsive functional group is:

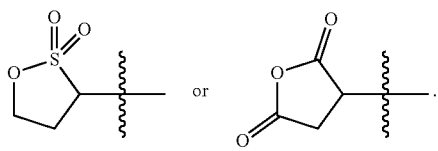 [SMILES: *C1CCOS1(=O)=O ; *C1CC(=O)OC1=O]

Suitable nucleophiles include primary alkyl amines and alkyl alcohols. An example of the sultone ring opening group and its ring opening reaction is as follows:

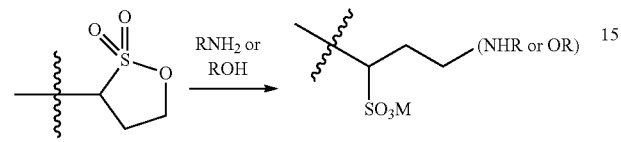

where M is H or a monovalent cation (sodium or potassium cation). The sultone ring opening group may be in a hydrophobic (or less hydrophilic) state, and when exposed to a high (basic) pH, may undergo a ring opening reaction and transition to a (more) hydrophilic state. The functional group after the ring opening reaction may also be anionic, and thus in a charged state.

In some aspects, the monomer comprising the nucleophile-responsive functional group is:

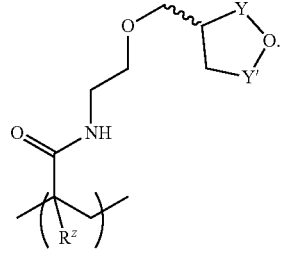

In particular examples, the monomer is:

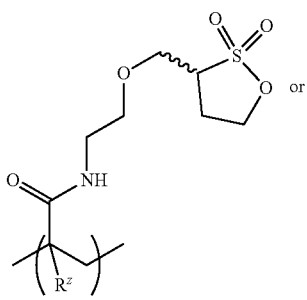

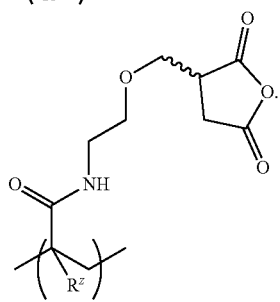

In some aspects, the nucleophile-responsive functional group may be attached to an acrylamide monomer, or an acrylate monomer, or a vinyl monomer. In some aspects, the switchable heteropolymer further comprises an acrylamide monomer. In some examples, the acrylamide monomer is an azido-containing acrylamide monomer. In some aspects, the switchable heteropolymer comprises:

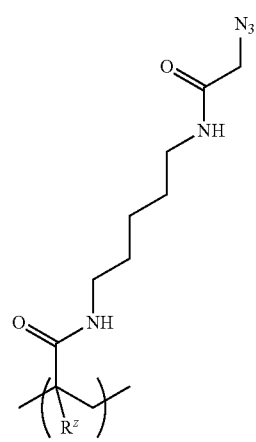

and optionally

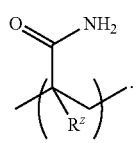

In some aspects, the heteropolymer has a structure:

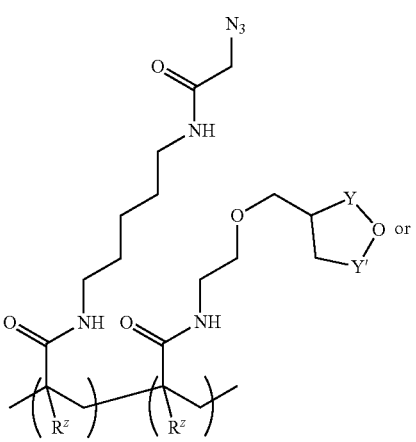

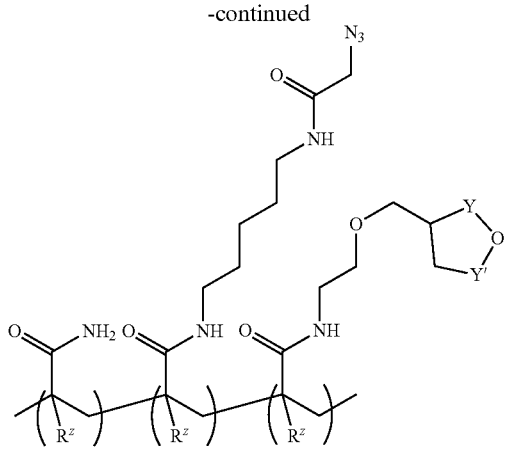

where each $R^z$ is independently H or $C_{1-4}$alkyl.

In some aspects, the stimuli-responsive functional group is a salt-responsive functional group. In some examples, the salt-responsive functional group is a zwitterionic functional group exhibiting antipolyelectrolyte behavior, wherein the zwitterionic functional group switches from a collapsed state to an extended state when exposed to a salt. The salt responsive functional group is a zwitterionic functional group having antipolyelectrolyte behavior. "Antipolyelectrolyte behavior," as used herein, means that the monomer including the zwitterionic functional group switches from a collapsed state to an extended state when exposed to a salt (i.e., the monomer possesses greater solubility in salt water than in pure water). As such, the salt responsive functional group may be in a collapsed state (e.g., where the polymer chains are in a globule), and when exposed to a salt solution, may transition to an extended state (i.e., where the polymer chains are extended). The impact of the local salt counterions changes the conformation of the polymer chain including the salt responsive functional group. In one example, a monomer including the zwitterionic functional group is selected from the group consisting of N-(2-methacryloyloxy)ethyl-N,N-dimethylammonio propanesulfonate and N-(3-methacryloylimino)propyl-N,N-dimethylammonio propanesulfonate.

In some examples, the monomer comprising the salt-responsive functional group has the structure:

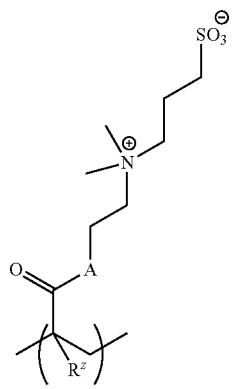

where A is O or NH and $R^z$ is H or $C_{1-4}$alkyl.

In other examples, salt-responsive functional groups are quaternary ammonium groups such as $—NMe_3^+$. An exemplary monomer is:

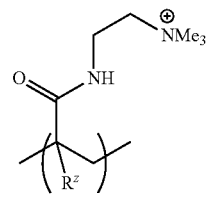

where $R^z$ is H or $C_{1-4}$alkyl.

When combined with an anionic counterpart (present in a salt solution), these charged materials may exhibit antipolyelectrolyte behavior. Examples of suitable anionic counterparts include a carboxylate salt, a sulfonate salt, a citrate salt, a phosphate salt, etc.

The salt responsive functional group may be attached to an acrylamide monomer, or an acrylate monomer, or a vinyl monomer. In some aspects, the switchable heteropolymer further comprises an acrylamide monomer. In some examples, the acrylamide monomer is an azido-containing acrylamide monomer. In some aspects, the switchable heteropolymer comprises:

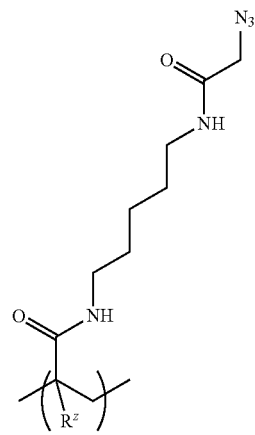

and optionally

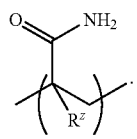

In some aspects, the heteropolymer has a structure:

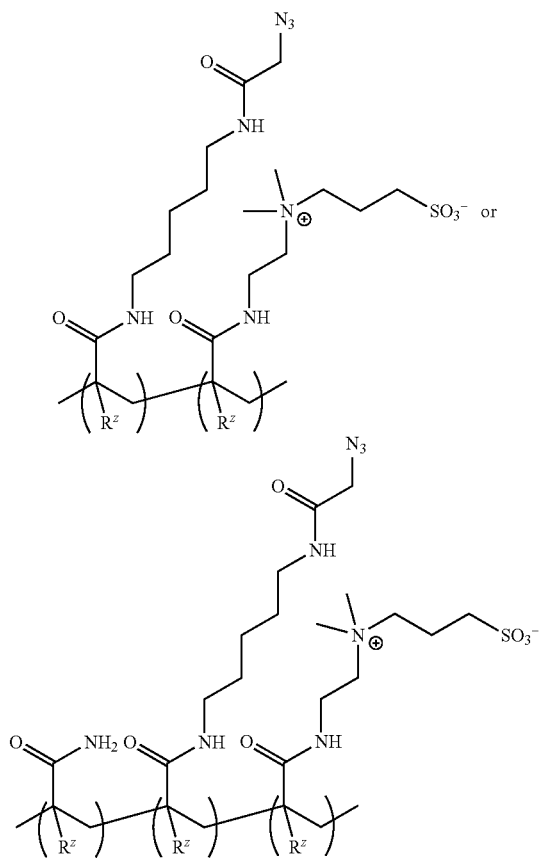

where each $R^z$ is independently H or $C_{1-4}$alkyl.

In one example, a flow cell comprises a support and a switchable heteropolymer attached to the support, wherein the stimuli-responsive functional group is selected from the group consisting of a pH-responsive functional group, a temperature-responsive functional group, a saccharide-responsive functional group, a nucleophile-responsive functional group, and a salt-responsive functional group. The stimuli-responsive functional group is capable of undergoing modification when exposed to a predetermined stimulus, wherein the modification changes the polarity and/or conformation of the switchable heteropolymer.

In some aspects, the flow cell support is a patterned substrate including depressions separated by interstitial regions, and wherein the heteropolymer is present within the depressions. In other aspects, the support is a non-patterned substrate having flow channel region and a bonding region, and wherein the heteropolymer is attached to the flow channel region.

In some aspects, the flow cell further comprises a primer grafted to the switchable heteropolymer.

In an example of this aspect of the flow cell, a surface of the support is functionalized with a silane or a silane derivative, and the heteropolymer is attached to the silane or the silane derivative. In some examples, the silane or silane derivative includes an unsaturated moiety that is capable of reacting with a functional group of the functionalized polymer layer. As used herein, the term "unsaturated moiety" refers to a chemical group which includes cycloalkenes, cycloalkynes, heterocycloalkenes, heterocycloalkynes, or optionally substituted variants thereof including at least one double bond or one triple bond. The unsaturated moieties can be mono-valent or di-valent. When the unsaturated moiety is mono-valent, cycloalkene, cycloalkyne, heterocycloalkene, and heterocycloalkyne are used interchangeably with cycloalkenyls, cycloalkynyls, heterocycloalkenyl, and heterocycloalkynyl, respectively. When the unsaturated moiety is di-valent, cycloalkene, cycloalkyne, heterocycloalkene, and heterocycloalkyne are used interchangeably with cycloalkenylene, cycloalkynylene, heterocycloalkenylene, and heterocycloalkynylene, respectively.

The unsaturated moiety can be covalently attached either directly to the silicon atoms of the silane or silane derivative, or indirectly attached via linkers. Examples of suitable linkers include optionally substituted alkylenes (e.g., bivalent saturated aliphatic radicals (such as ethylene) regarded as being derived from an alkene by opening of the double bond or from an alkane by removal of two hydrogen atoms from different carbon atoms), substituted polyethylene glycols, or the like.

The heteropolymers disclosed herein are made up of at least two different monomers. One of the monomers comprises a stimuli-responsive functional group. In some aspects, the other of the monomers includes an attachment group that may be reacted with the flow cell support and/or the primer to attach the heteropolymer thereto. This other attachment group may also be capable of attaching to the support, or the other monomer may include a second (different) attachment group that is capable of attaching to the support. It is to be understood that the polymers disclosed herein may also include one or more other monomers that do not interfere with the respective functions of the stimuli-responsive functional group and the attachment group.

In any examples of the polymer disclosed herein, the attachment group is selected from the group consisting of azido, amino, alkenyl (including cycloalkenyl or heterocycloalkenyl groups), alkynyl (including cycloalkynyl or heterocycloalkynyl groups), aldehyde, hydrazone, hydrazine, carboxyl, hydroxy, tetrazole, tetrazine, and thiol.

The attachment group may be capable of reacting with a functional group attached to the 5' end of the primer. For example, a bicyclo[6.1.0] non-4-yne (BCN) terminated primer may be captured by an azide attachment group of the polymer via strain-promoted catalyst free click chemistry. For another example, an alkyne terminated primer may be captured by an azide attachment group of the polymer via copper catalyzed click chemistry. For still another example, a norbornene terminated primer may undergo a catalyst-free ring strain promoted click reaction with a tetrazine attachment group of the polymer. It is to be understood that other coupling chemistries may be used to attach the primer to the attachment group, including, for example, Staudinger ligations, strain-promoted reactions, and photo-click cycloadditions.

Other examples of terminated primers that may be used include a tetrazine terminated primer, an azido terminated primer, an amino terminated primer, an epoxy or glycidyl terminated primer, a thiophosphate terminated primer, a thiol terminated primer, an aldehyde terminated primer, a hydrazine terminated primer, and a triazolinedione terminated primer.

In an example, the attachment group is attached to an acrylamide monomer. One example of the monomer that includes the attachment group is azido acetamido pentyl acrylamide.

In an example of the method, applying the polymer coating layer to a flow cell involves flow through deposition, chemical vapor deposition, dip coating, dunk coating, spin coating, spray coating, puddle dispensing, ultrasonic spray coating, doctor blade coating, aerosol printing, screen printing, microcontact printing, or inkjet printing.

In an example of the method, the flow cell support is a patterned flow cell support including depressions separated by interstitial regions, and the method further comprises: prior to applying the polymer coating layer, attaching a silane or a silane derivative to a surface of the patterned flow cell support, thereby forming silanized depressions and silanized interstitial regions; applying the polymer coating layer in the silanized depressions and on the silanized interstitial regions; and removing (e.g., polishing) the polymer coating layer from the silanized interstitial regions.

In an example of the method, exposing the polymer coating layer to the predetermined stimulus involves one of: heating the polymer coating layer; exposing the polymer coating layer to a solution of a predetermined pH; exposing the polymer coating layer to a nucleophile; exposing the polymer coating layer to a solution including a saccharide; or exposing the polymer coating layer to a salt solution.

In yet a further aspect, a method comprises exposing a polymer coating layer on at least a portion of a flow cell support to a predetermined stimulus, thereby causing a stimuli-responsive functional group of the polymer coating layer to switch i) from a current state to a more hydrophilic state than the current state, or ii) from a neutral state to a charged state, or iii) from a collapsed state to an extended state; and performing a sequencing operation using the flow cell support when the polymer coating layer is in the more hydrophilic state, the charged state, or the extended state.

In some aspects is a method for making the flow cells. The method includes applying a switchable heteropolymer to at least a portion of a flow cell support.

The addition of the polymer (polymer coating layer) and the primer (i.e., surface chemistry) to a patterned substrate will be described in reference to FIGS. 1A through 1F, and in FIGS. 1A through 1D in combination with FIGS. 1G and 1H, and the addition of the surface chemistry to the non-patterned substrate will be described in reference to FIGS. 2A through 2D.

FIG. 1A is a cross-sectional view of an example of the patterned support 12. The patterned support 12 may be a patterned wafer or a patterned die or any other patterned support (e.g., panel, rectangular sheet, etc.). Any example of the support 12 described herein may be used. The patterned wafer may be used to form several flow cells, and the patterned die may be used to form a single flow cell. In an example, the support may have a diameter ranging from about 2 mm to about 300 mm, or a rectangular sheet or panel having its largest dimension up to about 10 feet (~3 meters). In an example, the support wafer has a diameter ranging from about 200 mm to about 300 mm. In another example, the support die has a width ranging from about 0.1 mm to about 10 mm. While example dimensions have been provided, it is to be understood that supports/substrates with any suitable dimensions may be used. For another example, a panel may be used that is a rectangular support, which has a greater surface area than a 300 mm round wafer.

The patterned support 12 includes depressions 14 defined on or in an exposed layer or surface of the support 12, and interstitial regions 16 separating adjacent depressions 14. In the examples disclosed herein, the depressions 14 become functionalized with surface chemistry (e.g., 20, 22), while the interstitial regions 16 may be used for bonding but will not have primer(s) (shown in FIGS. 1E, 1F and 1H) present thereon.

The depressions 14 may be fabricated in or on the support 12 using a variety of techniques, including, for example, photolithography, nanoimprint lithography, stamping techniques, embossing techniques, molding techniques, micro-etching techniques, printing techniques, etc. As will be appreciated by those in the art, the technique used will depend on the composition and shape of the support 12.

Many different layouts of the depressions 14 may be envisaged, including regular, repeating, and non-regular patterns. In an example, the depressions 14 are disposed in a hexagonal grid for close packing and improved density. Other layouts may include, for example, rectilinear (i.e., rectangular) layouts, triangular layouts, and so forth. In some examples, the layout or pattern can be an x-y format of depressions 14 that are in rows and columns. In some other examples, the layout or pattern can be a repeating arrangement of depressions 14 and/or interstitial regions 16. In still other examples, the layout or pattern can be a random arrangement of depressions 14 and/or interstitial regions 16. The pattern may include spots, pads, wells, posts, stripes, swirls, lines, triangles, rectangles, circles, arcs, checks, plaids, diagonals, arrows, squares, and/or cross-hatches.

The layout or pattern may be characterized with respect to the density of the depressions 14 (i.e., number of depressions 14) in a defined area. For example, the depressions 14 may be present at a density of approximately 2 million per $mm^2$. The density may be tuned to different densities including, for example, a density of at least about 100 per $mm^2$, about 1,000 per $mm^2$, about 0.1 million per $mm^2$, about 1 million per $mm^2$, about 2 million per $mm^2$, about 5 million per $mm^2$, about 10 million per $mm^2$, about 50 million per $mm^2$, or more. Alternatively or additionally, the density may be tuned to be no more than about 50 million per $mm^2$, about 10 million per $mm^2$, about 5 million per $mm^2$, about 2 million per $mm^2$, about 1 million per $mm^2$, about 0.1 million per $mm^2$, about 1,000 per $mm^2$, about 100 per $mm^2$, or less. It is to be further understood that the density of depressions 14 on the support 12 can be between one of the lower values and one of the upper values selected from the ranges above. As examples, a high-density array may be characterized as having depressions 14 separated by less than about 100 nm, a medium density array may be characterized as having depressions 14 separated by about 400 nm to about 1 µm, and a low density array may be characterized as having depressions 14 separated by greater than about 1 µm. While example densities have been provided, it is to be understood that substrates with any suitable densities may be used.

The layout or pattern may also or alternatively be characterized in terms of the average pitch, i.e., the spacing from the center of the depression 14 to the center of an adjacent interstitial region 16 (center-to-center spacing). The pattern can be regular, such that the coefficient of variation around the average pitch is small, or the pattern can be non-regular in which case the coefficient of variation can be relatively large. In either case, the average pitch can be, for example, at least about 10 nm, about 0.1 m, about 0.5 m, about 1 m, about 5 m, about 10 m, about 100 m, or more. Alternatively or additionally, the average pitch can be, for example, at most about 100 m, about 10 m, about 5 µm, about 1 µm, about 0.5 µm, about 0.1 am, or less. The average pitch for a particular pattern of sites 16 can be between one of the lower values and one of the upper values selected from the ranges above. In an example, the depressions 14 have a pitch (center-to-center spacing) of about 1.5 µm. While example average pitch values have been provided, it is to be understood that other average pitch values may be used.

In the example shown in FIGS. 1A through 1H, the depressions 14 are wells 14', and thus the patterned support 12 includes an array of wells 14' in a surface thereof. The wells 14' may be micro wells or nanowells. The size of each well 14' may be characterized by its volume, well opening area, depth, and/or diameter.

Each well 14' can have any volume that is capable of confining a liquid. The minimum or maximum volume can be selected, for example, to accommodate the throughput (e.g., multiplexity), resolution, analyte composition, or analyte reactivity expected for downstream uses of the flow cell. For example, the volume can be at least about $1\times10^{-3}$ µm$^3$, about $1\times10^{-2}$ µm$^3$, about 0.1 µm$^3$, about 1 µm$^3$, about 10 µm$^3$, about 100 µm$^3$, or more. Alternatively or additionally, the volume can be at most about $1\times10^4$ µm$^3$, about $1\times10^3$ µm$^3$, about 100 µm$^3$, about 10 µm$^3$, about 1 µm$^3$, about 0.1 µm$^3$, or less. It is to be understood that the functionalized coating layer can fill all or part of the volume of a well 14'. The volume of the coating layer in an individual well 14' can be greater than, less than or between the values specified above.

The area occupied by each well opening on a surface can be selected based upon similar criteria as those set forth above for well volume. For example, the area for each well opening on a surface can be at least about $1\times10^{-3}$ m$^2$, about $1\times10^{-2}$ µm$^2$, about 0.1 µm$^2$, about 1 µm$^2$, about 10 µm$^2$, about 100 µm$^2$, or more. Alternatively or additionally, the area can be at most about $1\times10^3$ µm$^2$, about 100 µm$^2$, about 10 µm$^2$, about 1 µm$^2$, about 0.1 µm$^2$, about $1\times10^{-2}$ µm$^2$, or less. The area occupied by each well opening can be greater than, less than or between the values specified above.

The depth of each well 14' can be at least about 0.1 µm, about 1 µm, about 10 µm, about 100 µm, or more. Alternatively or additionally, the depth can be at most about $1\times10^3$ µm, about 100 µm, about 10 µm, about 1 µm, about 0.1 µm, or less. The depth of each well 14' can be greater than, less than or between the values specified above.

In some instances, the diameter of each well 14' can be at least about 50 nm, about 0.1 µm, about 0.5 µm, about 1 µm, about 10 µm, about 100 µm, or more. Alternatively or additionally, the diameter can be at most about $1\times10^3$ µm, about 100 µm, about 10 µm, about 1 am, about 0.5 µm, about 0.1 µm, or less (e.g., about 50 nm). The diameter of each well 14' can be greater than, less than or between the values specified above.

The patterned support 12 may be exposed to a series of processes in order to add the surface chemistry 20, 22 in the depression(s) 14.

While not shown, it is to be understood that the patterned support 12 may be exposed to a plasma ashing in order to clean and activate the surface. For example, the plasma ashing process may remove organic material and introduce surface hydroxyl groups. Other suitable cleaning processes may be used to clean the support 12, depending, in part, on the type of support 12. For example, chemical cleaning may be performed with oxidizing agents or caustic solutions.

Figure 1B:
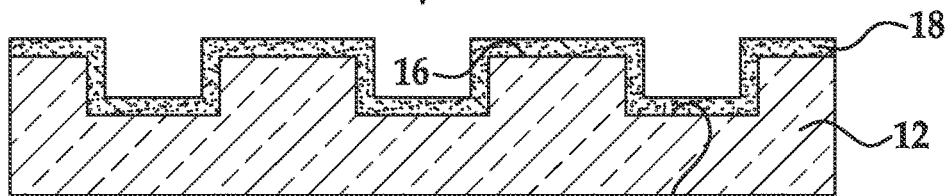
Figure 1C:
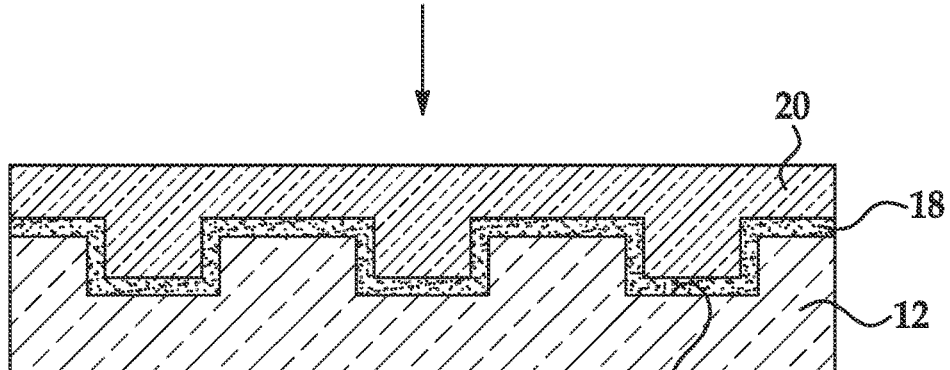

The patterned support 12 (shown in FIG. 1A) may then be exposed to a process that will prepare the surface for deposition of the stimuli-responsive polymer disclosed herein to form the polymer coating layer 20 (FIG. 1C). In an example, the patterned support 12 may be exposed to silanization, which attaches a silane or the silane derivative 18 (FIG. 1B) to the patterned support surface. Silanization introduces the silane or the silane derivative 18 across the surface, including in the depression 14, 14' (e.g., on the bottom surface and along the side walls) and on the interstitial regions 16. In some aspects, the silane or silane derivative is selectively introduced only to the depressions of a patterned substrate or to micro-locations (which are isolated from each other) of a non-patterned substrate.

Silanization may be accomplished using any silane or silane derivative 18. The selection of the silane or silane derivative 18 may depend, in part, upon the polymer that is to be used to form the polymer coating layer 20 (shown in FIG. 1C), as it may be desirable to form a covalent bond between the silane or silane derivative 18 and the polymer coating layer 20. The method used to attach the silane or silane derivative 18 to the support 12 may vary depending upon the silane or silane derivative 18 that is being used. Several examples are set forth herein.

In an example, the silane or silane derivative 18 is (3-aminopropyl)triethoxysilane (APTES) or (3-aminopropyl)trimethoxysilane (APTMS) (i.e., X—$R^B$—Si(O$R^C$)$_3$, wherein X is amino, $R^B$ is —(CH$_2$)$_3$—, and $R^C$ is ethyl or methyl). In this example, the support 12 surface may be pre-treated with the (3-aminopropyl)triethoxysilane (APTES) or (3-aminopropyl)trimethoxysilane (APTMS) to covalently link silicon to one or more oxygen atoms on the surface (without intending to be held by mechanism, each silicon may bond to one, two or three oxygen atoms). This chemically treated surface is baked to form an amine group monolayer. The amine groups are then reacted with Sulfo-HSAB to form an azido derivative. UV activation at 21° C. with 1 J/cm$^2$ to 30 J/cm$^2$ of energy generates an active nitrene species, which can readily undergo a variety of insertion reactions with the polymers disclosed herein.

Other silanization methods may also be used. Examples of suitable silanization methods include vapor deposition, a YES method, spin coating, or other deposition methods. Some examples of methods and materials that may be used to silanize the support 12 are described herein, although it is to be understood that other methods and materials may be used.

In an example utilizing the YES CVD oven, the patterned support 12 is placed in the CVD oven. The chamber may be vented and then the silanization cycle started. During cycling, the silane or silane derivative vessel may be maintained at a suitable temperature (e.g., about 120° C. for norbornene silane), the silane or silane derivative vapor lines be maintained at a suitable temperature (e.g., about 125° C. for norbornene silane), and the vacuum lines be maintained at a suitable temperature (e.g., about 145° C.).

In another example, the silane or silane derivative 18 (e.g., liquid norbornene silane) may be deposited inside a glass vial and placed inside a glass vacuum desiccator with a patterned support 12. The desiccator can then be evacuated to a pressure ranging from about 15 mTorr to about 30 mTorr, and placed inside an oven at a temperature ranging from about 60° C. to about 125° C. Silanization is allowed to proceed, and then the desiccator is removed from the oven, cooled and vented in air.

Vapor deposition, the YES method and/or the vacuum desiccator may be used with a variety of silane or silane derivative 18, such as those silane or silane derivatives 18 including examples of the unsaturated moieties disclosed herein. As examples, these methods may be used when the silane or silane derivative 18 includes a cycloalkene unsaturated moiety, such as norbornene, a norbornene derivative (e.g., a (hetero)norbornene including an oxygen or nitrogen in place of one of the carbon atoms), transcyclooctene, transcyclooctene derivatives, transcyclopentene, transcycloheptene, trans-cyclononene, bicyclo[3.3.1]non-1-ene, bicyclo[4.3.1]dec-1 (9)-ene, bicyclo[4.2.1]non-1(8)-ene, and bicyclo[4.2.1]non-1-ene. Any of these cycloalkenes can be substituted, for example, with an R group, such as hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An example of the norbornene derivative includes [(5-bicyclo[2.2.1]hept-2-enyl)ethyl]trimethoxysilane. As other examples, these methods may be used when the silane or silane derivative 18 includes an alkyne or cycloalkyne unsaturated moiety, such as cyclooctyne, a cyclooctyne derivative, or bicyclononynes (e.g., bicyclo[6.1.0]non-4-yne or derivatives thereof, bicyclo[6.1.0]non-2-yne, or bicyclo[6.1.0]non-3-yne). These cycloalkynes can be substituted with any of the R groups described herein.

As shown in FIG. 1B, the attachment of the silane or silane derivative 18 forms a silanized patterned support, including silanized depressions and silanized interstitial regions (which are one example of the treated depressions and treated interstitial regions).

The silanized patterned support may then be exposed to a process that will form the polymer coating layer 20 on the silanized depressions and silanized interstitial regions.

Prior to applying the polymer coating layer 20, some examples of the method may involve synthesizing a heteropolymer that is to be deposited to form the polymer coating layer 20. The synthesizing may involve copolymerizing a stimuli-responsive functional group containing monomer with a monomer selected from the group consisting of azido acetamido pentyl acrylamide monomer and a combination of an acrylamide monomer and the azido acetamido pentyl acrylamide monomer. Any of the pH-responsive, temperature-responsive, saccharide-responsive, nucleophile-responsive, or salt-responsive monomers described herein may be used to form the heteropolymers. Several approaches could be used to make the polymer materials disclosed herein. As a few examples, the polymerization method used may be free radical polymerization, controlled radical polymerization, a non-radical method, or another suitable method.

As described herein, examples of the polymer coating layer 20 include any of the stimuli-responsive polymers disclosed herein which include any example of the stimuli-responsive functional group and any example of the attachment group. The stimuli-responsive polymer may be present in or incorporated into a mixture. In an example, the mixture includes the stimuli-responsive polymer in an ethanol and water mixture. The polymer coating layer 20 may be formed on the surface of the silanized patterned support 12 (i.e., onto the silanized depressions and the silanized interstitial regions) using any suitable technique. The stimuli-responsive polymer may be deposited on the surface of the patterned support 12 using chemical vapor deposition (CVD), or dipping or dip coating, dunk coating, spin coating, spray coating or ultrasonic spray coating, puddle dispensing, doctor blade coating, aerosol printing, screen printing, microcontact printing, or inkjet printing, or via other suitable techniques. The polymer coating layer 20 is shown in FIG. 1C.

Dunk coating may involve submerging the patterned and silanized support into a series of temperature controlled baths. The baths may also be flow controlled and/or covered with a nitrogen blanket. The baths may include the polymer mixture. Throughout the various baths, the stimuli-responsive polymer will attach to form the polymer coating layer 20 in the silanized depression(s) and on the interstitial regions. In an example, the patterned and silanized support will be introduced into a first bath including the polymer mixture where a reaction takes place to attach the polymer, and then the patterned, silanized, and polymer coated support will be moved to additional baths for washing. The patterned support may be moved from bath to bath with a robotic arm or manually. A drying system may also be used in dunk coating.

Spray coating may be accomplished by spraying the polymer mixture directly onto the patterned and silanized support. The spray coated support may be incubated for a time sufficient to attach the polymer. After incubation, any unattached polymer mixture may be diluted and removed using, for example, a spin coater or by sonication in a bath or dunk tank described herein.

Puddle dispensing may be performed according to a pool and spin off method, and thus may be accomplished with a spin coater. The polymer mixture may be applied (manually or via an automated process) to the patterned and silanized support. The applied polymer mixture may be applied to or spread across the entire surface of the patterned and silanized support. The polymer coated patterned support may be incubated for a time a time sufficient to attach the polymer. After incubation, any unattached polymer mixture may be diluted and removed using, for example, the spin coater or by sonication in a bath or dunk tank described herein.

The attachment of the polymer coating layer 20 to the silanized depressions and silanized interstitial regions (i.e., 18) may be through covalent bonding. The covalent linking of the polymer coating layer 20 to the silanized depressions is helpful for maintaining the polymer coating layer 20 in the depressions 14, 14' throughout the lifetime of the ultimately formed flow cell during a variety of uses. The following are some examples of reactions that can take place between the silane or silane derivative 18 and the polymer coating layer 20.

When the silane or silane derivative 18 includes norbornene or a norbornene derivative as an unsaturated moiety, the norbornene or a norbornene derivative can: i) undergo a 1,3-dipolar cycloaddition reaction with an azide/azido group of the stimuli-responsive polymer; ii) undergo a coupling reaction with a tetrazine group attached to the stimuli-responsive polymer; iii) undergo a cycloaddition reaction with a hydrazone group attached to the stimuli-responsive polymer; iv) undergo a photo-click reaction with a tetrazole group attached to the stimuli-responsive polymer; or v) undergo a cycloaddition with a nitrile oxide group attached to the stimuli-responsive polymer.

When the silane or silane derivative 18 includes cyclooctyne or a cyclooctyne derivative as the unsaturated moiety, the cyclooctyne or cyclooctyne derivative can: i) undergo a strain-promoted azide-alkyne 1,3-cycloaddition (SPAAC) reaction with an azide/azido of the stimuli-responsive polymer, or ii) undergo a strain-promoted alkyne-nitrile oxide cycloaddition reaction with a nitrile oxide group attached to the stimuli-responsive polymer.

When the silane or silane derivative 18 includes a bicyclononyne as the unsaturated moiety, the bicyclononyne can undergo similar SPAAC alkyne cycloaddition with azides or nitrile oxides attached to the stimuli-responsive polymer due to the strain in the bicyclic ring system.

While not shown, it is to be understood that in some examples of the method, the patterned support 12 may not be exposed to silanization. Rather, the patterned support 12 may be exposed to plasma ashing, and then the polymer coating layer 20 may be directly spin coated (or otherwise deposited) on the plasma ashed patterned support 12. In this example, plasma ashing may generate surface-activating agent(s) (e.g., —OH groups, as a hydroxyl or carboxyl) that can adhere the polymer coating layer 20 to the patterned support 12. In these examples, the other functional group of the polymer coating layer 20 may be selected so that it reacts with the surface groups generated by plasma ashing. For example, the other functional group of the polymer coating layer 20 may be an N-hydroxysuccinimide ester (NHS ester).

After being coated, the stimuli-responsive polymer may also be exposed to a curing process to form the polymer coating layer 20 across the entire patterned substrate (i.e., on depression(s) 14 and interstitial region(s) 16). In an example, curing the stimuli-responsive polymer may take place at a temperature ranging from room temperature (e.g., about 25° C.) to about 60° C. for a time ranging from about 5 minutes to about 2 hours.

The silanized and coated patterned substrate (shown in FIG. 1C) may be exposed to a cleaning process. This process may utilize a water bath and sonication. The water bath may be maintained at a relatively low temperature ranging from about 22° C. to about 45° C. In another example the water bath temperature ranges from about 25° C. to about 30° C.

Figure 1D:
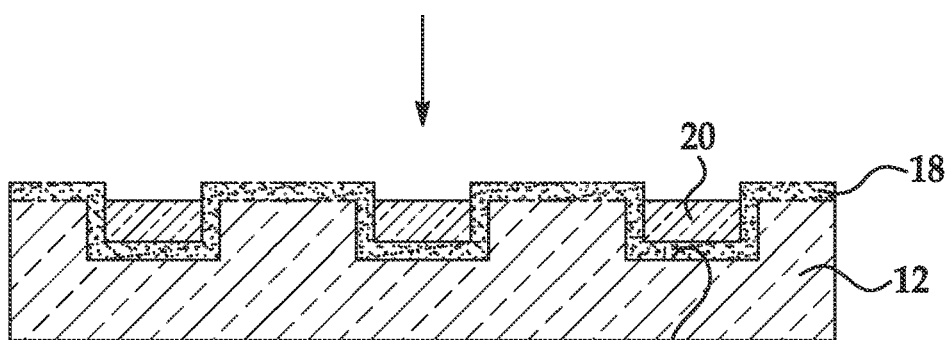

The silanized and coated patterned support is then exposed to polishing, if needed, to remove portion(s) of the polymer coating layer 20 from the silanized interstitial regions. The silanized, coated, and polished patterned substrate is shown in FIG. 1D. The portions of the silane or silane derivative 18 that are adjacent to the interstitial regions 16 may or may not be removed as a result of polishing. As such, in FIGS. 1D through 1H, the portions of the silane or silane derivative 18 that are adjacent to the interstitial regions 16 are shown in phantom, as they may at least partially remain after polishing or they may be removed after polishing. When these silanized portions are completely removed, it is to be understood that the underlying support 12 is exposed.

The polishing process may be performed with a gentle chemical slurry (including, e.g., an abrasive, a buffer, a chelating agent, a surfactant, and/or a dispersant) which can remove the thin polymer coating layer 20, and in some instances, at least part of the silane or silane derivative 18, from the interstitial regions 16 without deleteriously affecting the underlying support 12 at those regions. Alternatively, polishing may be performed with a solution that does not include the abrasive particles.

The chemical slurry may be used in a chemical mechanical polishing system to polish the surface of the silanized and coated patterned support shown in FIG. 1C. The polishing head(s)/pad(s) or other polishing tool(s) is/are capable of polishing the polymer coating layer 20 from the interstitial regions 16 while leaving the polymer coating layer 20 in the depressions 14, 14' and leaving the underlying support 12 at least substantially intact. As an example, the polishing head may be a Strasbaugh ViPRR II polishing head.

As mentioned above, polishing may be performed with a polishing pad and a solution without any abrasive. For example, the polish pad may be utilized with a solution free of the abrasive particle (i.e., a solution that does not include abrasive particles).

Polishing removes portion(s) of the polymer coating layer 20 (and in some instances at least part of the silane or silane derivative 18) from the interstitial regions 16 and leaves portion(s) of the polymer coating layer 20 in the silanized depressions, as shown in FIG. 1D. Also as mentioned above, the interstitial region(s) 16 may remain silanized after polishing is complete. In other words, the silanized interstitial regions may remain intact after the polishing. Alternatively (as indicated by the phantom portions of 18), the silane or silane derivative 18 may be removed from the interstitial region(s) 16 as a result of polishing.

While not shown, it is to be understood that the silanized, coated, and polished patterned support (shown in FIG. 1D) may be exposed to a cleaning process. This process may utilize a water bath and sonication. The water bath may be maintained at a relatively low temperature ranging from about 22° C. to about 30° C. The silanized, coated, and polished patterned substrate may also be spin dried, or dried via another suitable technique.

Figure 1E:
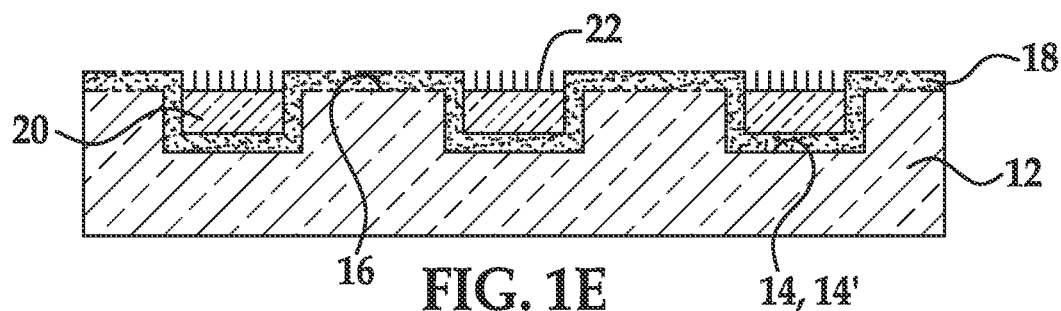
Figure 1F:
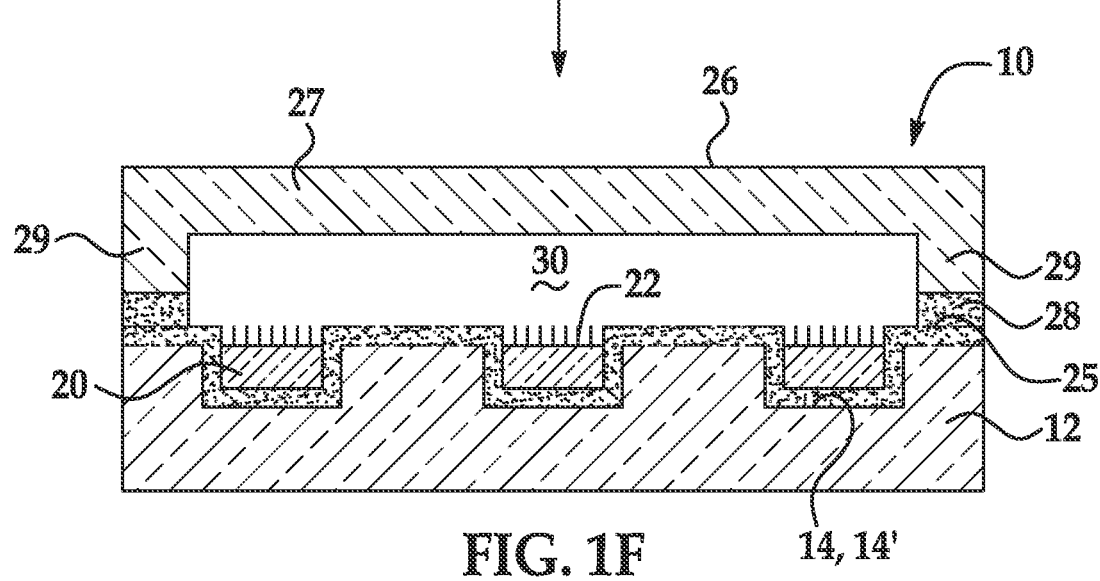
Figure 1G:
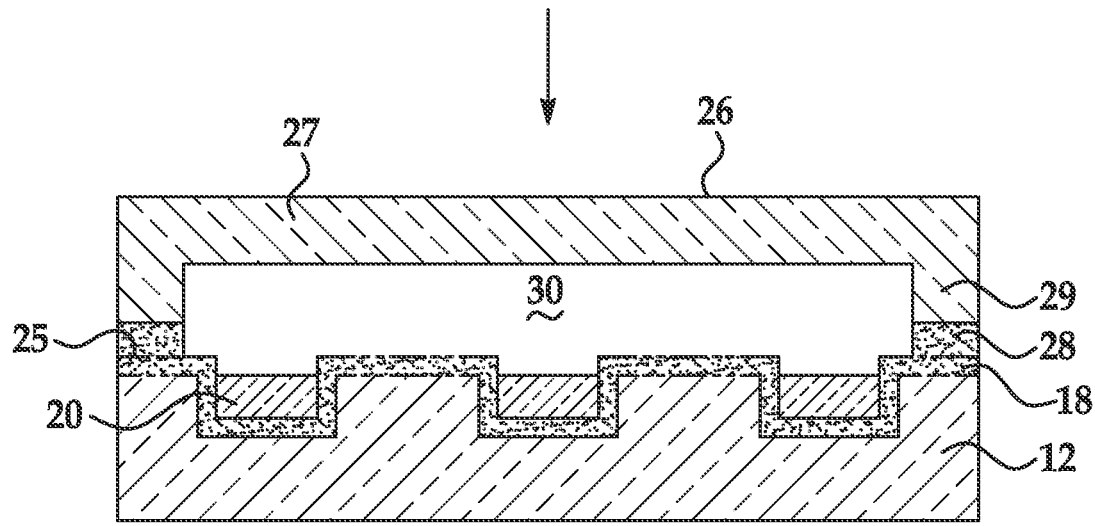
Figure 1H:
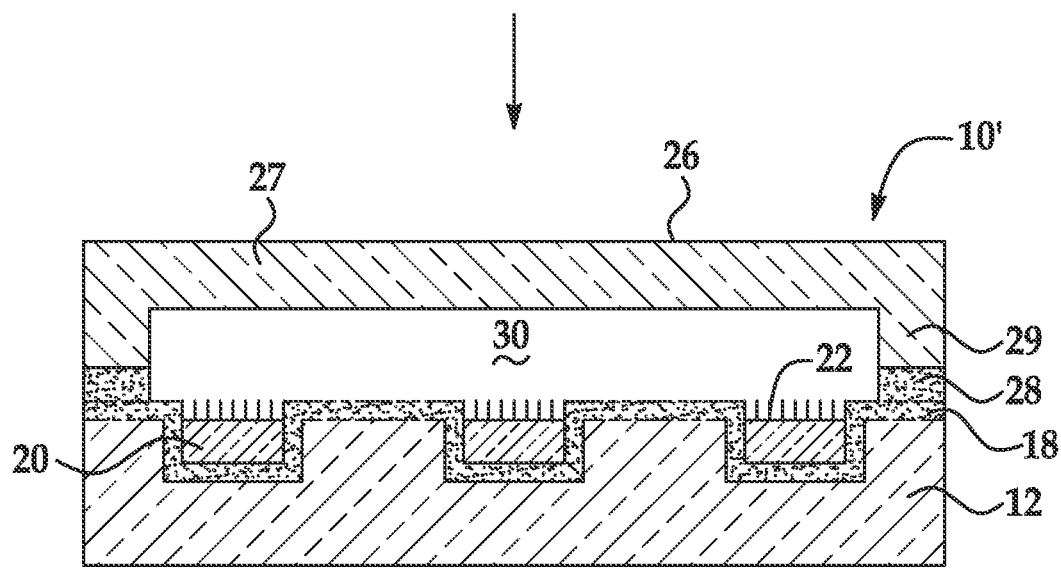

The silanized, coated, and polished patterned support shown in FIG. 1D may then be exposed to the processes shown in FIGS. 1E and 1F, which generate the flow cell 10, or to the processes shown in FIGS. 1G and 1H, which generate the flow cell 10'. In FIGS. 1E and 1F, the primers 22 are grafted before the lid 26 is bonded to the patterned flow cell support 12. In FIGS. 1G and 1H, the lid 26 is bonded to the patterned flow cell support 12 before the primers 22 are grafted.

In FIG. 1E, a grafting process is performed in order to graft the primer 22 to the polymer coating layer 20 in the depression(s) 14, 14'. The primer 22 may be any forward amplification primer or reverse amplification primer that includes the alkyne functional group. Specific examples of suitable primers include P5 and/or P7 primers, which are used on the surface of commercial flow cells sold by Illumina, Inc., for sequencing on HISEQ™ HISEQX™, MISEQ™, MISEQDX™, MINISEQ™, NEXTSEQ™, NEXTSEQDX™ NOVASEQ™, GENOME ANALYZER™, ISEQ™, and other instrument platforms.

In this example, grafting may be accomplished by flow through deposition (e.g., using a temporarily bound lid), dunk coating, spray coating, puddle dispensing, or by another suitable method that will attach the primer(s) 22 to the functionalized polymer layer 20 in at least some of the depressions 14, 14'. Each of these example techniques may utilize a primer solution or mixture, which may include the primer(s), water, a buffer, and a catalyst, and may be performed as described herein.

Dunk coating may involve submerging the patterned support (having the polymer coating layer 20 in the depression(s) 14 thereof) into a series of temperature controlled baths. The baths may also be flow controlled and/or covered with a nitrogen blanket. The baths may include the primer solution or mixture. Throughout the various baths, the primer(s) 22 will attach to the attachment group(s) of the polymer coating layer 20 in at least some of the depression(s) 14. In an example, the coated and polished patterned support will be introduced into a first bath including the primer solution or mixture where a reaction takes place to attach the primer(s), and then the patterned substrate will be moved to additional baths for washing. The patterned substrate may be moved from bath to bath with a robotic arm or manually. A drying system may also be used in dunk coating.

Spray coating may be accomplished by spraying the primer solution or mixture directly onto the coated and polished patterned support. The spray coated wafer may be incubated for a time ranging from about 4 minutes to about 60 minutes at a temperature ranging from about 0° C. to about 70° C. After incubation, the primer solution or mixture may be diluted and removed using, for example, a spin coater.

Puddle dispensing may be performed according to a pool and spin off method, and thus may be accomplished with a spin coater. The primer solution or mixture may be applied (manually or via an automated process) to the coated and polished patterned support. The applied primer solution or mixture may be applied to or spread across the entire surface of the coated and polished patterned support. The primer coated patterned substrate may be incubated for a time ranging from about 2 minutes to about 60 minutes at a temperature ranging from about 0° C. to about 80° C. After incubation, the primer solution or mixture may be diluted and removed using, for example, the spin coater.

As depicted in FIG. 1F, the lid 26 may then be bonded to a bonding region 25 of the support 12. When the patterned flow cell support 12 is a wafer, different areas of the lid 26 may at least partially define respective flow channels 30 that are being formed using the wafer. When the patterned flow cell support 12 is a die, the lid 26 may define the one or more flow channels 30 that is/are being formed.

The lid 26 may be any material that is transparent to an excitation light that is directed toward the surface chemistry 20, 22 in the depression(s) 14. As examples, the lid 26 may be glass (e.g., borosilicate, fused silica, etc.), plastic, or the like. A commercially available example of a suitable borosilicate glass is D 263®, available from Schott North America, Inc. Commercially available examples of suitable plastic materials, namely cyclo olefin polymers, are the ZEONOR® products available from Zeon Chemicals L.P.

In some examples, the lid 26 may be integrally formed with sidewall(s) 29 that correspond with the shape of the bonding region 25, and that will be bonded to the bonding region 25. For example, a recess may be etched into a transparent block to form a substantially planar (e.g., top) portion 27 and sidewall(s) 29 extending from the substantially planar portion 27. When the etched block is mounted to the bonding region of the patterned substrate 12, the recess may become the flow channel 30.

In other examples, the sidewall(s) 29 and the lid 26 may be separate components that are coupled to each other. For example, the lid 26 may be a substantially rectangular block having an at least substantially planar exterior surface and an at least substantially planar interior surface that defines a portion (e.g., a top portion) of the flow channel 30 (once bonded to the patterned support 12). The block may be mounted onto (e.g., bonded to) the sidewall(s) 29, which are bonded to the bonding region 25 of the patterned flow cell substrate 12 and form sidewall(s) of the flow channel 30. In this example, the sidewall(s) 29 may include any of the materials set forth herein for the spacer layer (described below).

The lid 26 may be bonded to the bonding region 25 of the patterned flow cell support 12 using any suitable technique, such as laser bonding, diffusion bonding, anodic bonding, eutectic bonding, plasma activation bonding, glass frit bonding, or others methods known in the art. In an example, a spacer layer 28 may be used to bond the lid 26 to the bonding region 25. The spacer layer 28 may be any material that will seal at least some of the interstitial regions 16 (e.g., the bonding region 25) of the patterned substrate 12 and the lid 26 together.

In one example, the spacer layer 28 may be a radiation-absorbing material that absorbs radiation at a wavelength that is transmitted by the lid 26 and/or the patterned support 12. The absorbed energy, in turn, forms the bond between the spacer layer 28 and the lid 26 and between the spacer layer 28 and the patterned substrate 12. An example of this radiation-absorbing material is black KAPTON® (polyimide containing carbon black) from DuPont (USA), which absorbs at about 1064 nm. It is to be understood that polyimide could be used without the addition of carbon black, except that the wavelength would have to be altered to one that is significantly absorbed by the natural polyimide material (e.g., 480 nm). As another example, polyimide CEN JP can be bonded when irradiated with light at 532 nm. When the spacer layer 28 is the radiation-absorbing material, the spacer layer 28 may be positioned at an interface between the lid 26 and the patterned support 12 so that the spacer layer 28 contacts the desired bonding region 25. Compression may be applied (e.g., approximately 100 PSI of pressure) while laser energy at a suitable wavelength is applied to the interface (i.e., the radiation-absorbing material is irradiated). The laser energy may be applied to the interface both from the top and from the bottom in order to achieve suitable bonding.

In another example, the spacer layer 28 may include a radiation-absorbing material in contact therewith. The radiation-absorbing material may be applied at the interface between the spacer layer 28 and the lid 26 as well as at the interface between the spacer layer 28 and the patterned flow cell support 12. As an example, the spacer layer 28 may be polyimide and the separate radiation-absorbing material may be carbon black. In this example, the separate radiation-absorbing material absorbs the laser energy that forms the bonds between the spacer layer 28 and the lid 26 and between the spacer layer 28 and the patterned support 12. In this example, compression may be applied at the respective interfaces while laser energy at a suitable wavelength is applied to the interfaces (i.e., the radiation-absorbing material is irradiated).

When the patterned flow support 12 is a wafer, the spacer layer 28 and sidewalls 29 (of or connected to the lid 26) may physically separate one flow channel 30 from an adjacent flow channel 30 and may be located at the periphery of the wafers. When the patterned support 12 is a die and the flow cell 10 that is being formed is to include a single flow channel 30 or lane, the spacer layer 28 and sidewalls 29 (of or connected to the lid 26) may be located at the periphery of the die to define the flow channel 30 and seal the flow cell 10. When the patterned support 12 is a die and the flow cell 10 that is being formed is to include multiple isolated flow channels 30 (e.g., eight or four flow channels/lanes), the spacer layer 28 and sidewalls 29 (of or connected to the lid 26) may physically separate one flow channel/lane 30 from an adjacent flow channel/lane 30 and may be located at the periphery of the die. It is to be understood, however, that the spacer layer 28 and sidewalls 29 may be located in any desired region depending on the implementation.

When the patterned support 12 is a die, assembling the flow cell 10 may involve the bonding of the lid 26. When the patterned support 12 is a wafer, assembling the flow cell 10 may involve additional processing, such as dicing, after the lid 26 is bonded. In one example, the lid 26 may be bonded to the patterned wafer, and dicing forms individual flow cells 10. As mentioned herein, on a wafer, the sidewalls 29 may physically separate one flow channel 30 from an adjacent flow channel 30, and thus dicing may take place through at least some of the sidewalls 29, so that each individual flow cell 10 includes a desirable number of flow channels 30, each of which has a portion of the original sidewall 29 surrounding its periphery. In another example, the patterned wafer may be diced to form non-lidded dies, which can have respective lids 26 bonded thereto to form individual flow cells 10.

In the example flow cell 10 shown in FIG. 1F, the lid 26 includes the top portion 27 integrally formed with sidewall(s) 29. The sidewall(s) 29 are bonded to the bonding region 25 of the patterned substrate 12 through the spacer layer 28.

Together, the lid 26 and the patterned flow cell substrate 12 define the flow channel 30, which is in selective fluid communication with the depressions 14, 14'. The flow channel 30 may serve to, for example, selectively introduce reaction components or reactants to the surface chemistry 20, 22 in order initiate designated reactions in/at the depressions 14, 14'.

Prior to performing a sequencing operation, the flow cell 10 may be exposed to the predetermined stimulus of the polymer coating layer 20 in order to transition the polymer coating layer 20 from a current state to a more hydrophilic state (e.g., from the hydrophobic state to the hydrophilic state), from the neutral state to the charged state, and/or from the collapsed state to the expanded state. The predetermined stimulus used will depend upon the polymer coating layer 20 and the stimuli-responsive functional group that it includes. Exposing the polymer coating layer 20 to the predetermined stimulus may involve heating the polymer coating layer 20; exposing the polymer coating layer 20 to a solution of a predetermined pH; exposing the polymer coating layer 20 to a solution including a saccharide; exposing the polymer coating layer 20 to a nucleophile; or exposing the polymer coating layer 20 to a salt solution. When the lid 26 is attached, exposing the polymer coating layer 20 to any of the solutions may be accomplished by a flow through process. For example, a basic or acidic solution, a saccharide solution (e.g., glucose), or a salt solution may be introduced into the flow cell channel 30 through an input port, allowed to incubate for a time sufficient for the desired property change to take place, and then removed from the channel 30 through an output port. In an example, the incubation time may be from seconds to several minutes. When the stimuli-responsive functional group is thermo-responsive, the entire flow cell 10 could be heated, or a heated solution may be exposed to the polymer coating layer 20 using the flow through process.

The predetermined stimulus will render the polymer coating layer 20 more compatible with the conditions of the subsequently performed sequencing operation.

Examples of the solutions of the predetermined pH may include basic solutions, such as 0.1 M NaOH, TRIS-HCL buffer, or a carbonate buffer, or acidic solutions, such as citrate buffer (pH 6) or 2-(N-morpholino)ethanesulfonic acid (MES) buffer. An example of a saccharide solution includes a glucose solution having a concentration ranging from about 1 mM to about 100 mM. Examples of the salt solution include saline-sodium citrate buffer and phosphate buffered saline (PBS) buffer.

Referring now to FIGS. 1G and 1H, another example of the method includes bonding the lid 26 to the patterned flow cell support 12 before the primers 22 are grafted.

As shown in FIG. 1G, the polymer coating layer 20 has been applied (e.g., deposited and polished) as described in FIG. 1D. At least some of the polished interstitial regions 16 may define the bonding region 25, and the lid 26 may be bonded to the bonding region 25. The lid 26 may be any of the materials and may have any of the configurations described herein. The lid 26 may be bonded to the bonding region 25 via any of the techniques described herein.

In the example shown in FIG. 1G, the lid 26 includes a top portion 27 integrally formed with sidewall(s) 29. The sidewall(s) 29 are bonded to the bonding region 25 of the patterned substrate 12 through the spacer layer 28. After the lid 26 is bonded, the flow channel 30 is formed between the lid 26 and the patterned substrate 12. The flow channel 30 may serve to selectively introduce various fluids to the flow cell 10' (FIG. 1H).

In this example, the primer 22 is then grafted to the polymer coating layer 20 in the depression(s) 14, as shown in FIG. 1H. Any of the primers 22 described herein may be used. In this example, grafting may be accomplished by a flow through process. In the flow through process, the primer solution or mixture described herein may be introduced into the flow channel(s) 30 through respective input port(s) (not shown), may be maintained in the flow channel(s) 30 for a time sufficient (i.e., an incubation period) for the primer 22 to attach to the polymer coating layer 20 in one or more of the depressions 14, and then may be removed from respective output port(s) (not shown). After primer 22 attachment, the additional fluid(s) may be directed through the flow channel(s) 30 to wash the now functionalized depressions and the flow channel(s) 30.

Prior to performing a sequencing operation, the flow cell 10' may be exposed to the predetermined stimulus of the polymer coating layer 20 in order to transition the polymer coating layer 20 from the current (e.g., more hydrophobic) state to the more hydrophilic state than the current state, the neutral state to the charged state, and/or the collapsed state to the expanded state. The predetermined stimulus used will depend upon the polymer coating layer 20 and the stimuli-responsive functional group that it includes. Exposing the polymer coating layer 20 to the predetermined stimulus may involve heating the polymer coating layer 20; exposing the polymer coating layer 20 to a solution of a predetermined pH; exposing the polymer coating layer 20 to a solution including a saccharide; exposing the polymer coating layer 20 to a nucleophile; or exposing the polymer coating layer 20 to a salt solution. When the lid 26 is attached, exposing the polymer coating layer 20 to any of the solutions may be accomplished by a flow through process as previously described herein. When the stimuli-responsive functional group is thermo-responsive, the entire flow cell 10' could be heated, or a heated solution may be exposed to the polymer coating layer 20 using the flow through process.

The predetermined stimulus will render the polymer coating layer 20 more compatible with the conditions of the subsequently performed sequencing operation.

In other examples, exposing the polymer coating layer 20 to the predetermined stimulus may take place prior to primer 22 grafting. In examples in which predetermined stimulus exposure takes place prior to primer 22 grafting at FIG. 1E, techniques other than the flow through process, such as dip or dunk coating may be used. For example, the silanized, coated, and polished patterned support shown in FIG. 1D may be dipped into a basic or acidic solution, a saccharide solution (e.g., glucose), or a salt solution for a time sufficient for the desired property change to take place. For another example, the silanized, coated, and polished patterned support shown in FIG. 1D may be heated to a desired temperature to initiate the state transition. In examples in which predetermined stimulus exposure takes place prior to primer 22 grafting at FIG. 1H, the flow through process may be used for such exposure. For another example, the silanized, coated, and polished patterned support having the lid 26 attached thereto, as shown in FIG. 1G, may be heated to a desired temperature to initiate the state transition. Heating may be performed in the presence of water or a buffer.

As mentioned above, the surface chemistry 20, 22 may also be added to a non-patterned support, and this example will be described in reference to FIGS. 2A through 2D. With a non-patterned support 12', a continuous surface would include the same surface chemistry 20, 22 that is found in the wells 14' of FIGS. 1E, 1F, and 1H. Any of the supports disclosed herein may be used as the non-patterned substrate 12', except the non-patterned substrate 12' does not include depressions 14 or interstitial regions 16. In this example method, the lid 26 (shown in FIG. 2B) is bonded to the non-patterned substrate 12' at the outset to form the flow channel(s) 30. The lid 26 may be any of the materials and in any of the configurations described herein. The lid 26 may also be bonded to the non-patterned substrate 12' via any of the techniques described herein.

Figure 2A:
FIGS. 2A through 2D are schematic cross-sectional views depicting another example of the method disclosed herein.
Figure 2B:
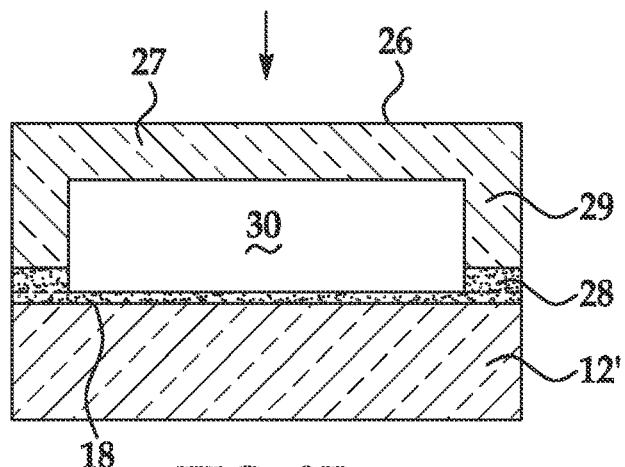

In the example shown in FIG. 2B, the lid 26 includes a top portion 27 integrally formed with sidewall(s) 29. The sidewall(s) 29 are bonded to a bonding region 25 of the non-patterned substrate 12' through the spacer layer 28. The bonding region 25 may be at a periphery of the non-patterned substrate 12', or at any areas where it is desirable to form a boundary of a flow channel 30. In other examples, the spacer layer 28 may form the sidewall(s) and may be attached to an at least substantially planar lid 26.

Together, the lid 26 (including the sidewall(s) 29) and the non-patterned substrate 12' define the flow channel 30. The flow channel 30 may serve to, for example, selectively introduce fluids in order to form the surface chemistry 20, 22 and to selectively introduce reaction components or reactants to the surface chemistry 20, 22 in order to initiate a state transition of the polymer coating layer 20 and/or to initiate other designated reactions within the flow channel 30.

Prior to forming the polymer coating layer 20 (shown in FIG. 2C), the method may involve exposing the non-patterned substrate 12' (via a flow through process) to a cleaning process and/or to another process (e.g., silanization) that prepares the exposed surface of the non-patterned substrate 12' for the subsequent deposition of the stimuli-responsive polymer.

Silanization of the non-patterned substrate 12' is shown in FIG. 2B. In this example, silanization attaches the silane or the silane derivative 18 to the exposed portions of the non-patterned wafer surface 12' that are present in the flow channel 30.

Silanization may be accomplished using any silane or silane derivative 18. The selection of the silane or silane derivative 18 may depend, in part, upon the stimuli-responsive polymer that is to be used to form the polymer coating layer 20 (shown in FIG. 2C), as it may be desirable to form a covalent bond between the silane or silane derivative 18 and the polymer coating layer 20. The method used to attach the silane or silane derivative 18 to the substrate 12' may be a flow through process.

Figure 2C:
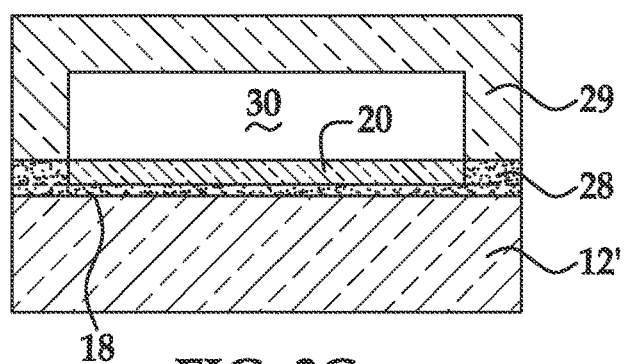

As shown in FIG. 2C, in this example, the polymer coating layer 20 is then formed on the silane or silane derivative 18, or on other chemistry that has been deposited to prepare the exposed surface of the non-patterned substrate 12' within the flow channel 30.

Any of the stimuli-responsive polymers described herein may be used, and combinations of the stimuli-responsive polymers may be used together. In an example, the polymer coating layer formation may be accomplished by a flow through process. In the flow through process, the stimuli-responsive polymer(s) may be introduced into the flow channel(s) 30 through respective input port(s) and may or may not be cured. The polymer coating layer 20 will form on the exposed surface of the non-patterned substrate 12' and polishing does not take place.

Figure 2D:
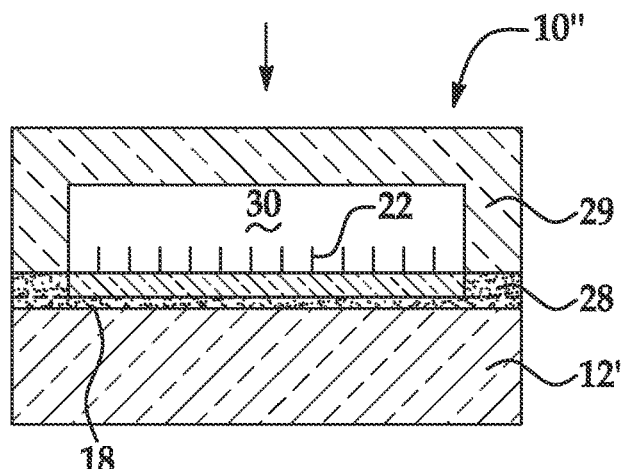

As shown in FIG. 2D, the primer 22 is grafted to the polymer coating layer 20 in the flow channel 30. In this example, grafting may be accomplished by a flow through process. In the flow through process, a primer solution or mixture may be introduced into the flow channel(s) 30 through respective input port(s), may be maintained in the flow channel(s) for a time sufficient (i.e., an incubation period) for the primer 22 to attach to the attachment group of the polymer coating layer 20. The remaining primer solution or mixture may then be removed from respective output port(s). After primer attachment, the additional fluid(s) may be directed through the flow channel(s) to wash the now functionalized flow channel(s) 30. The resulting flow cell 10" in this example is shown in FIG. 2D.

Prior to performing a sequencing operation, the flow cell 10" may be exposed to the predetermined stimulus of the polymer coating layer 20 in order to transition the polymer coating layer 20 from a current state to a more hydrophilic state (e.g., from the hydrophobic state to the hydrophilic state, from a hydrophilic state to a more hydrophilic state), the neutral state to the charged state, and/or the collapsed state to the expanded state. The predetermined stimulus used will depend upon the polymer coating layer 20 and the stimuli-responsive functional group that it includes. Exposing the polymer coating layer 20 to the predetermined stimulus may involve heating the polymer coating layer 20; exposing the polymer coating layer 20 to a solution of a predetermined pH; exposing the polymer coating layer 20 to a solution including a saccharide; exposing the polymer coating layer 20 to a nucleophile; or exposing the polymer coating layer 20 to a salt solution. Because the lid 26 is attached, exposing the polymer coating layer 20 to any of the solutions may be accomplished by a flow through process as previously described herein. When the stimuli-responsive functional group is thermo-responsive, the entire flow cell 10" could be heated, or a heated solution may be exposed to the polymer coating layer 20 using the flow through process.

The predetermined stimulus will render the polymer coating layer 20 more compatible with the conditions of the subsequently performed sequencing operation. A sequencing operation is the process of determining the order nucleotides in a sample of DNA or RNA. In an example, the sequencing operation is sequencing by synthesis, which involves imaging a fluorescently labeled reversible terminator as a nucleotide is added to a template strand, and then cleaving the fluorescently labeled reversible terminator to allow for incorporation of the next base.

In other examples using the flow cell 10", exposing the polymer coating layer 20 to the predetermined stimulus may take place prior to primer 22 grafting. Again, because the lid 26 is attached prior to application of the polymer coating layer 20, the flow through process may be used for the predetermined stimulus exposure. For another example, the silanized and coated non-patterned support, as shown in FIG. 2C, may be heated to a desired temperature to initiate the state transition. Heating may be accomplished in an aqueous environment (e.g., water or a buffer).

While not shown, it is to be understood that the patterned support 12 or non-patterned support 12' may include inlet and outlet ports that are to fluidically engage other ports (not shown) for directing fluid(s) into the respective flow channels (e.g., from a reagent cartridge or other fluid storage system) and out of the flow channel (e.g., to a waste removal system).

Also while not shown, it is to be understood that instead of being bonded to a lid 26, a functionalized support (with surface chemistry, 20, 22 thereon) may be bonded to another functionalized substrate with surface chemistry, 20, 22 thereon. The two functionalized surfaces can face each other and can have a flow channel defined therebetween. A spacer layer and suitable bonding method may be used to bond two of the functionalized substrates together.

The flow cells 10, 10', 10" disclosed herein may be used in a variety of sequencing approaches or technologies, including techniques often referred to as sequencing-by-synthesis (SBS), cyclic-array sequencing, sequencing-by-ligation, pyrosequencing, and so forth. With any of these techniques and in examples using a patterned support 12, since the polymer coating layer 20 and attached primer(s) 22 are present in the functionalized depressions (i.e., 14, 14' with surface chemistry 20, 22 thereon) and not on the interstitial regions 16, amplification will be confined to the functionalized depressions. Sequencing generally involves hybridizing a nucleic acid template to the flow cell, amplifying the nucleic acid template, and detecting a signal when a nucleotide or an oligonucleotide associates with the amplified nucleic acid template.

As one example, a sequencing by synthesis (SBS) reaction may be run on a system such as the HISEQ™, HISEQX™, MISEQ™, MISEQDX™, MINISEQ™, NOVASEQ™ NEXTSEQDX™, or NEXTSEQ™ sequencer systems from Illumina (San Diego, CA).

An SBS sequencing operation generally includes introducing a nucleic acid library template to the flow cell support 12, whereby the nucleic acid library template hybridizes to a primer 22 attached to the polymer coating layer 20; generating a nucleic acid template strand from the hybridized nucleic acid library template; introducing a sequencing primer that is complementary to an adapter of the nucleic acid template strand; introducing fluorescently labeled nucleotides and a polymerase to the flow cell support 12, whereby one of the fluorescently labeled nucleotides is incorporated to extend the sequencing primer along the nucleic acid template strand; and detecting a fluorescent signal from the incorporated one of the fluorescently labeled nucleotides.

In SBS, a plurality of nucleic acid library templates may be introduced to the flow cell 10, 10', 10". Multiple nucleic acid library templates are hybridized, for example, to one of two types of primers 22 immobilized on the flow cell 10, 10', 10". Cluster generation may then be performed. In one example of cluster generation, the nucleic acid library templates are copied from the hybridized primers 22 by 3' extension using a high-fidelity DNA polymerase. The original nucleic acid library templates are denatured, leaving the copies immobilized where primers 22 are located. Isothermal bridge amplification may be used to amplify the immobilized copies. For example, the copied templates loop over to hybridize to an adjacent, complementary primer 22, and a polymerase copies the copied templates to form double stranded bridges, which are denatured to form two single stranded strands. These two strands loop over and hybridize to adjacent, complementary primers 22 and are extended again to form two new double stranded loops. The process is repeated on each template copy by cycles of isothermal denaturation and amplification to create dense clonal clusters. Each cluster of double stranded bridges is denatured. In an example, the reverse strand is removed by specific base cleavage, leaving forward template strands.

The 3' end of the templates and any primers 22 can be blocked to prevent unwanted priming. The sequencing primer can be introduced to the flow cell 10, 10', 10". Because the sequencing primer is complementary to an adapter of the nucleic acid template strand, it will hybridize to the adapter (e.g., a read 1 sequencing primer of the template).

Extension of a nucleic acid primer (e.g., the sequencing primer) along the nucleic acid template (e.g., the forward template polynucleotide strand) is monitored to determine the sequence of nucleotides in the template. The underlying chemical process can be polymerization (e.g., catalyzed by a polymerase enzyme) or ligation (e.g., catalyzed by a ligase enzyme). In a particular polymerase-based SBS process, fluorescently labeled nucleotides are added to the template (thereby extending the sequencing primer) in a template dependent fashion such that detection of the order and type of nucleotides added to the sequencing primer can be used to determine the sequence of the template. For example, to initiate a first SBS cycle, one or more labeled nucleotides, DNA polymerase, etc., may be delivered into/through the flow channel 30, etc. that houses an array of primers 22 having template strands attached thereto. Sequencing primer extension causes a labeled nucleotide to be incorporated, and this incorporation can be detected through an imaging event. During an imaging event, an illumination system (not shown) may provide an excitation light to the flow cell 10, 10', 10".

In some examples, the nucleotides can further include a reversible termination property that terminates further sequencing primer extension once a nucleotide has been added. For example, a nucleotide analog having a reversible terminator moiety can be added to the sequencing primer along the template strand such that subsequent extension cannot occur until a deblocking agent is delivered to remove the moiety. Thus, for examples that use reversible termination, a deblocking reagent can be delivered to the flow channel 30, etc. (before or after detection occurs).

Wash(es) may take place between the various fluid delivery steps. The SBS cycle can then be repeated n times to extend the sequencing primer by n nucleotides, thereby detecting a sequence of length n.

While SBS has been described in detail, it is to be understood that the flow cells 10, 10', 10" described herein may be utilized with other sequencing protocols, such as flowcell-based library preparation, for genotyping, or in other chemical and/or biological applications.

To further illustrate the present disclosure, example and prophetic examples are given herein. It is to be understood that these examples are provided for illustrative purposes and are not to be construed as limiting the scope of the disclosure.

NON-LIMITING WORKING EXAMPLES AND PROPHETIC EXAMPLES

Example 1. Synthesis of a Saccharide-Responsive Switchable Heteropolymer (Boronic Acid)

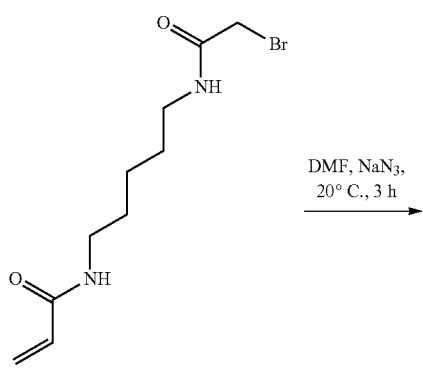

43

-continued

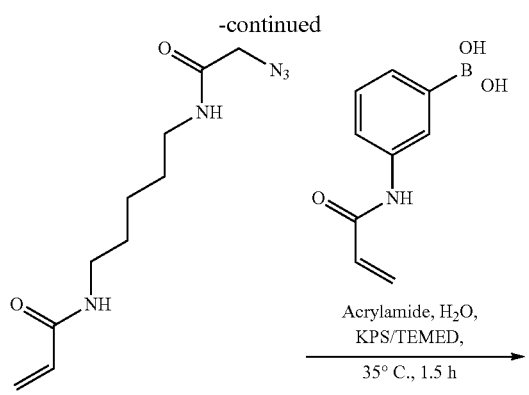

x:y:z, ~85:~5:~10

A mixture of BrAPA (N-(5-bromoacetamidylpentyl)acrylamide), sodium azide, and dimethylformamide (DMF) was placed in a DrySyn bath and the solution heated under a nitrogen atmosphere with stirring for 3 h at 20° C. to form AzAPA (N-(5-azidoacetamidylpentyl) acrylamide). Acrylamide and 3-(acrylamido)phenylboronic acid were dissolved in deionized water. The prepared AzAPA solution was then added to the acrylamide/3-(acrylamido)phenylboronic acid solution and mixed thoroughly before being filtered through a 0.2 μm filter. The filtered solution was then transferred to a 500 mL round-bottomed flask equipped with a stirrer bar and nitrogen was bubbled through the mixture for 30 min. Whilst degassing the acrylamide/AzAPA premix, the required quantity of potassium persulfate in deionized water was prepared and was then transferred to the mixture of monomers. The mixture was then treated with the co-initiator TEMED (Tetramethylethylenediamine). The solution was stirred under nitrogen at 35° C. for 1.5 h. At the end of the polymerization, the nitrogen gas line was removed to expose the reaction flask to air. The crude mixture was then added slowly to 2-propanol. The crude polymer was then isolated by filtration.

44

Prophetic Example 2. Synthesis of pH-Responsive Switchable Heteropolymer (Anionic)

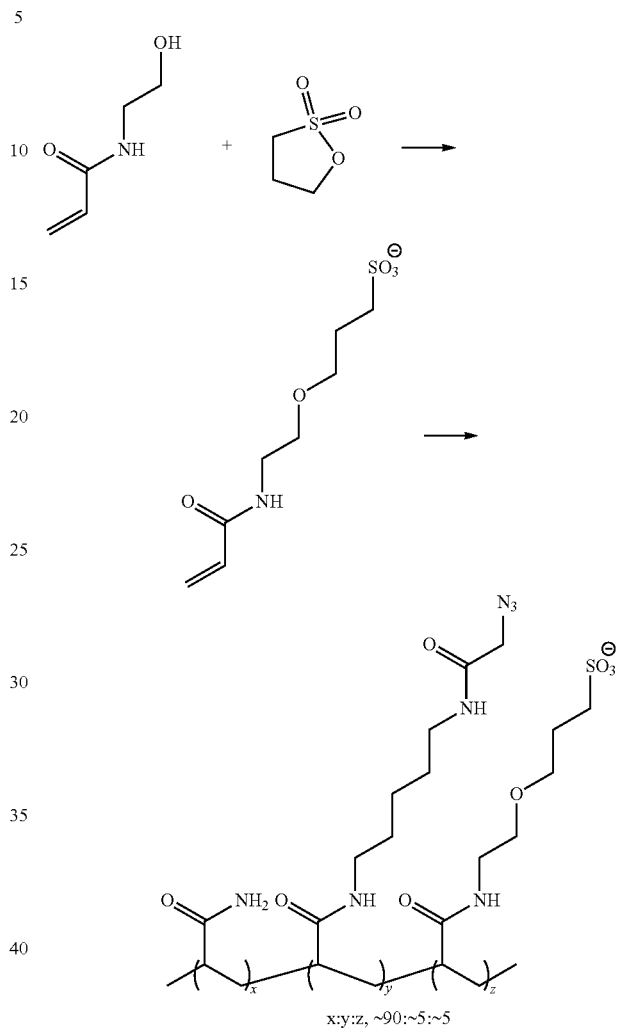

x:y:z, ~90:~5:~5

A mixture of the acrylate derivative and sultone is reacted to form the sulfonate-derivatized acrylate monomer. The monomer is converted to the heteropolymer as described in Example 1.

Prophetic Example 3. Synthesis of Nucleophile-Responsive Switchable Heteropolymer (Sultone)

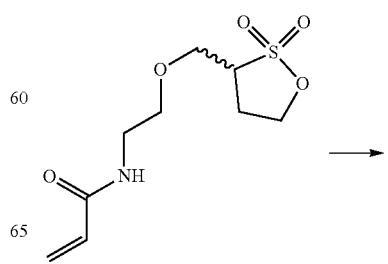

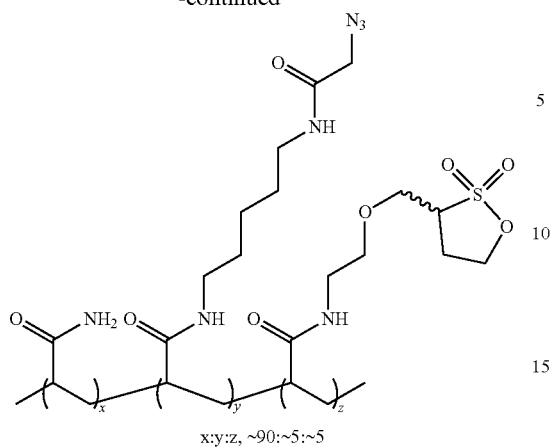

x:y:z, ~90:~5:~5

The sultone-derivatized acrylate monomer is converted to the heteropolymer as described in Example 1.

Prophetic Example 4. Synthesis of a Nucleophile-Responsive Switchable Heteropolymer (Cyclic Anhydride)

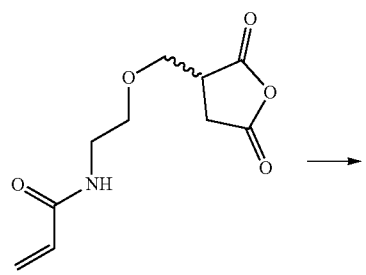

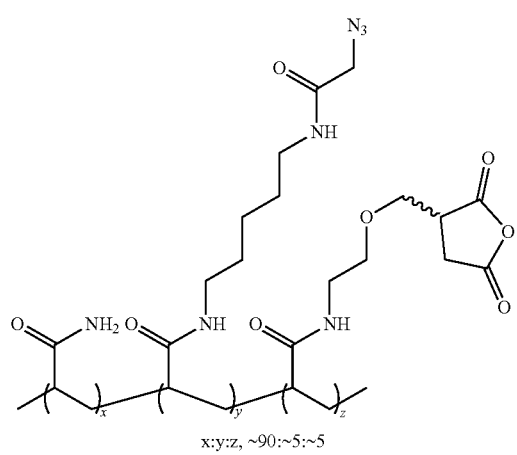

x:y:z, ~90:~5:~5

The succinic anhydride-derivatized acrylate monomer is converted to the heteropolymer as described in Example 1.

Example 5. Synthesis of a Salt-Responsive Switchable Heteropolymer (Zwitterionic)

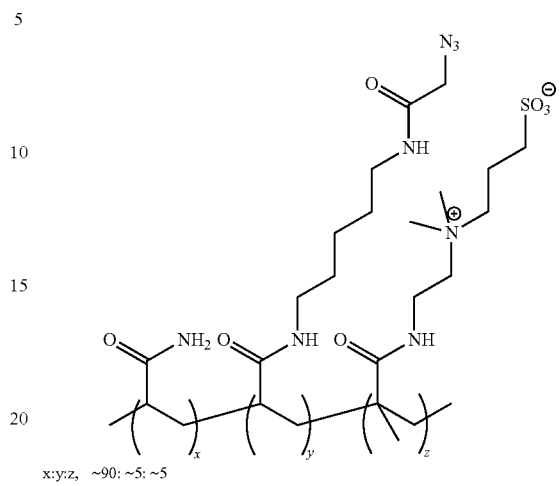

x:y:z, ~90: ~5: ~5

The heteropolymer shown was prepared from the appropriate monomers as described in Example 1. This heteropolymer may have improved dry storage robustness.

Example 6. Synthesis of a pH-Responsive Switchable Heteropolymer (Anionic)

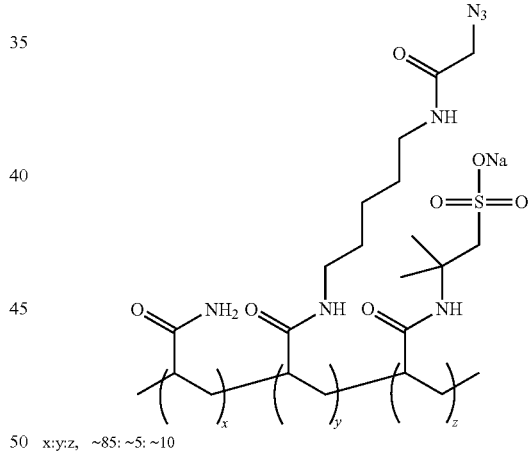

x:y:z, ~85: ~5: ~10

The heteropolymer shown was prepared from the appropriate monomers as described in Example 1. This heteropolymer may have improved dry storage robustness.

Example 7. Sequencing Operations Using Switchable Heteropolymers

Four heteropolymers were respectively coated on the surface of the channels of four single-channel, non-patterned, flow cells using a flow through process.
    Control: poly(N-(5-azidoacetamidylpentyl)acrylamide-co-acrylamide), also known as PAZAM)
    Test 1: Zwitterionic switchable heteropolymer of Example 5
    Test 2: Anionic switchable heteropolymer of Example 6

Test 3: Saccharide switchable heteropolymer of Example 1

18-26 μM primers were grafted on each of the polymer layers in the separate flowcells.

Prior to sequencing, the Example 1 polymer was exposed to a solution of glucose, which transitioned the Example 1 polymer from its neutral and relatively hydrophobic state, to its negatively charged and more hydrophilic state. In this example, the Example 5 polymer and the Example 6 polymer were not switched.

Figure 3A:
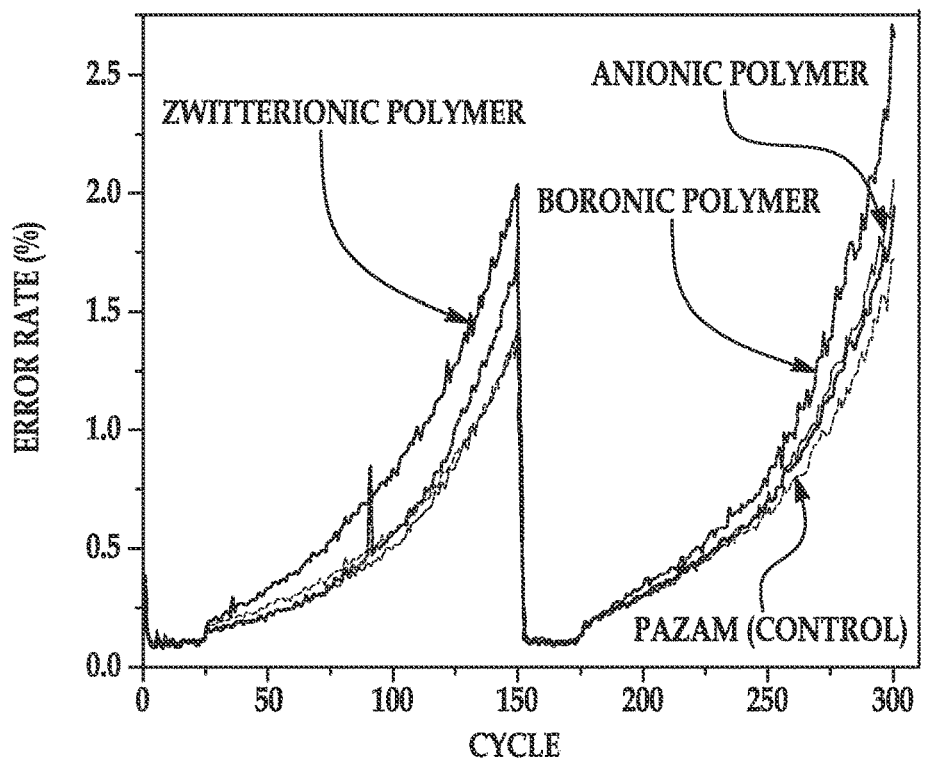
FIGS. 3A and 3B are graphs depicting error rate percentage (FIG. 3A) and quality metric percentage (FIG. 3B) for flow cells formed with comparative polymers and an example of the polymer disclosed herein.
Figure 3B:
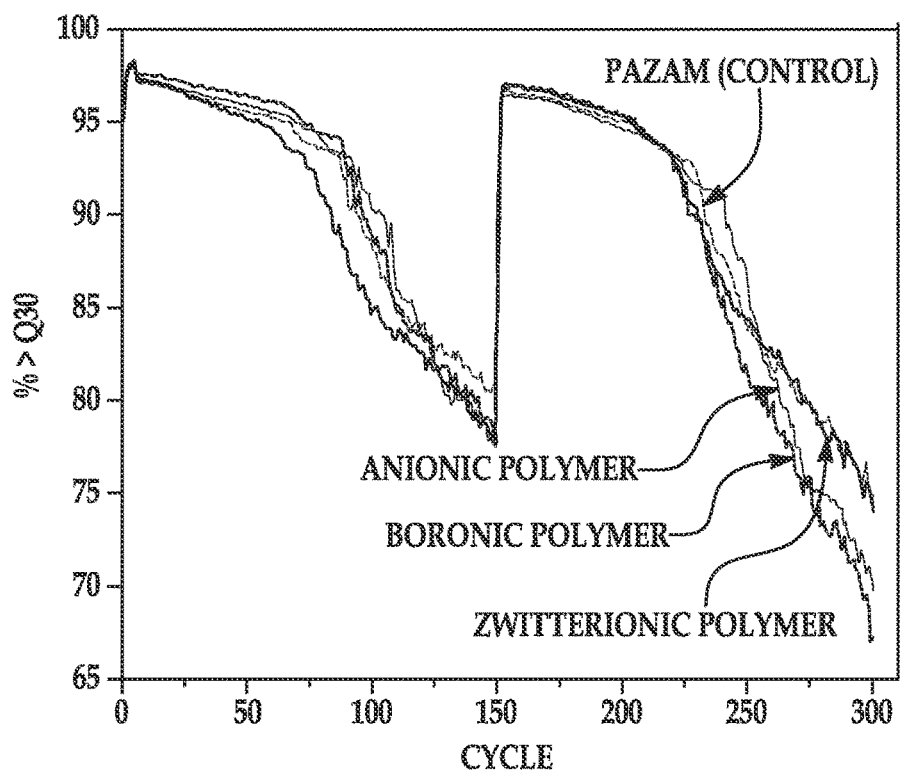

More than 300 sequencing cycles were performed in each of the channels using a PhiX library. Read 1 corresponds with cycles 1-151 and Read 2 corresponds with cycles 152-302. The sequencing data collected included error rate (percentage) (shown in FIG. 3A) and quality score (percentage greater than Q30) (shown in FIG. 3B). Q30 is equivalent to the probability of an incorrect base call 1 in 1000 times. This means that the base call accuracy (i.e., the probability of a correct base call) is 99.9%. A lower base call accuracy of 99% (Q20) will have an incorrect base call probability of 1 in 100, meaning that every 100 base pair sequencing read will likely contain an error. When sequencing quality reaches Q30, virtually all of the reads will be perfect, having zero errors and ambiguities. As shown in FIGS. 3A and 3B, each of the Example polymers performed similarly to the comparative/control example. These results indicate that the Example 1, 4 and 5 polymers are capable of supporting a sequencing-by-synthesis technique with the performance being approximately matched to the performance of the control example. It is believed that similar results may be obtained with all types of sequencing libraries.

Additional Notes

It should be appreciated that all combinations of the concepts described herein and in the appended claims (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

While several examples have been described in detail, it is to be understood that the disclosed examples may be modified. Therefore, the foregoing description is to be considered non-limiting.

What is claimed is:

1. A heteropolymer, comprising:
   an acrylamide monomer comprising a tetrazine attachment group to react with a functional group attached to a primer; and
   a monomer comprising a stimuli-responsive functional group, wherein the monomer comprising the stimuli-responsive functional group is selected from the group consisting of:
      an acrylamide monomer including a terminal pH-responsive functional group selected from the group consisting of a hydroxyl with an acid-labile protecting group, a hydroxyl with a base-labile protecting group, 1,2-diol protected as an acetal, hemiacetal, or ketal, 1,3-diol protected as an acetal, hemiacetal, or ketal, a tert-butyloxycarbonylamino group (boc), a 9H-fluoren-9-ylmethoxycarbonylamino group (Fmoc), a carboxylate group, a carboxylic acid group, a sulfonate group, and a sulfonic acid group;
      a vinyl or acrylate monomer including a terminal pH-responsive functional group selected from the group consisting of a hydroxyl with an acid-labile protecting group, a hydroxyl with a base-labile protecting group, an amino with an acid-labile protecting group, an amino with a base-labile protecting group, a sulfonate group and a sulfonic acid group;
      a temperature-responsive N-substituted acrylamide;
      an acrylamide, acrylate, or vinyl monomer including a terminal saccharide-responsive functional group;
      an acrylamide, acrylate, or vinyl monomer including a terminal nucleophile-responsive functional group; and
      an acrylamide, acrylate, or vinyl monomer including a terminal salt-responsive functional group.

2. The heteropolymer of claim 1, wherein the monomer comprising the stimuli-responsive functional group is to undergo modification when exposed to a predetermined stimulus, wherein the modification changes the polarity and/or conformation of the heteropolymer.

3. The heteropolymer of claim 1, further comprising the primer grafted to the attachment group.

4. The heteropolymer of claim 1, wherein:
   the monomer comprising the stimuli-responsive functional group is the acrylamide, acrylate, or vinyl monomer including the terminal saccharide-responsive functional group; and
   the terminal saccharide-responsive functional group comprises a boronic acid group.

5. The heteropolymer of claim 4, wherein the monomer comprising the stimuli-responsive functional group is 3-(acrylamido)phenylboronic acid.

6. The heteropolymer of claim 1, wherein:
   the monomer comprising the stimuli-responsive functional group is the acrylamide, acrylate, or vinyl monomer including the terminal nucleophile-responsive functional group; and
   the terminal nucleophile-responsive functional group has the following structure:

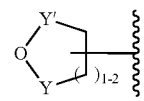

wherein: (a) Y is SO2 and Y' is CH2; or (b) Y and Y' are both C(O).

7. The heteropolymer of claim 1, wherein:
   the monomer comprising the stimuli-responsive functional group is the acrylamide, acrylate, or vinyl monomer including the terminal salt-responsive functional group; and
   the salt-responsive functional group is a zwitterionic functional group exhibiting antipolyelectrolyte behavior.

8. The heteropolymer of claim 7, wherein the monomer comprising the stimuli-responsive functional group has one of the following structures:

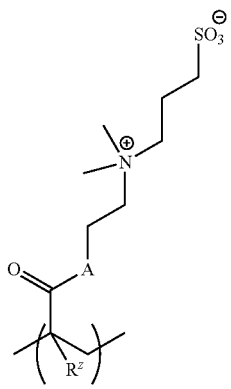

(i)

wherein A is O or NH and Rz is H or C1-4alkyl; or

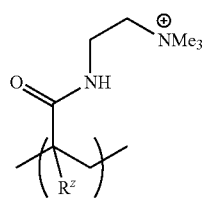

(ii)

wherein Rz is H or C1-4alkyl.

9. The heteropolymer of claim 1, wherein:

the monomer comprising the stimuli-responsive functional group is the temperature-responsive N-substituted acrylamide; and the temperature-responsive N-substituted acrylamide includes a heat-sensitive hydroxyl or amino protecting group.

10. The heteropolymer of claim 1, wherein:

the monomer comprising the stimuli-responsive functional group is the temperature-responsive N-substituted acrylamide; and the temperature-responsive N-substituted acrylamide is N-isopropylacrylamide.

11. A flow cell, comprising:

a support; and the heteropolymer of claim 1 attached to the support.

12. A method of making a flow cell, comprising contacting the heteropolymer of claim 1 with at least a portion of a flow cell support, thereby attaching the heteropolymer to the flow cell support.

13. The method of claim 12, further comprising grafting a primer to the attachment group of the heteropolymer attached to the support.

14. The method of claim 12, further comprising exposing the heteropolymer attached to the flow cell support to a predetermined stimulus.

15. The method of claim 14, further comprising, after the exposing, performing a sequencing operation on the flow cell.

16. The heteropolymer of claim 1, wherein the acrylamide monomer including the terminal pH-responsive functional group has a structure:

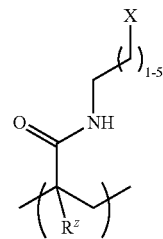

where:

X is —O-Boc, —NHBoc, or —NHFmoc; and each $R^z$ is independently H or $C_{1-4}$alkyl.

* * * * *